United States Patent
Dunn

(10) Patent No.: US 9,014,847 B2
(45) Date of Patent: Apr. 21, 2015

(54) SYSTEMS FOR POINT-OF-USE MEDICATION CONTROL

(76) Inventor: Lawrence A. Dunn, Durham, NC (US)

( * ) Notice: Subject to any disclaimer, the term of this patent is extended or adjusted under 35 U.S.C. 154(b) by 0 days.

(21) Appl. No.: 12/953,738

(22) Filed: Nov. 24, 2010

(65) Prior Publication Data

US 2011/0125318 A1 May 26, 2011

Related U.S. Application Data

(62) Division of application No. 11/649,471, filed on Jan. 4, 2007, now Pat. No. 7,885,725.

(60) Provisional application No. 60/756,372, filed on Jan. 5, 2006.

(51) Int. Cl.
- G06F 17/00 (2006.01)
- G06F 19/00 (2011.01)
- G07F 9/02 (2006.01)

(52) U.S. Cl.
CPC ............ G06F 19/3462 (2013.01); G07F 9/026 (2013.01); G07F 9/02 (2013.01)

(58) Field of Classification Search
CPC .................................. G07F 9/02; G07F 9/026
USPC .......................................... 700/237, 236, 243
See application file for complete search history.

(56) References Cited

U.S. PATENT DOCUMENTS

| | | |
|---|---|---|
| 4,695,954 A | 9/1987 | Rose et al. |
| 4,698,954 A | 10/1987 | Behr et al. |
| 4,744,492 A | 5/1988 | Hackmann et al. |
| 5,047,948 A | 9/1991 | Turner |
| 5,127,543 A | 7/1992 | Meisels |
| 5,292,029 A * | 3/1994 | Pearson ............................ 221/2 |
| 5,329,459 A | 7/1994 | Kaufman et al. |
| 5,408,443 A | 4/1995 | Weinberger |
| 5,480,062 A | 1/1996 | Rogers |
| 5,571,258 A | 11/1996 | Pearson |
| 5,582,323 A | 12/1996 | Kurtenbach |
| 5,646,912 A | 7/1997 | Cousin |
| 5,657,236 A | 8/1997 | Conkright |

(Continued)

FOREIGN PATENT DOCUMENTS

| | | |
|---|---|---|
| EP | 2 672 947 | 12/2013 |
| WO | WO 2012/109222 A2 | 8/2012 |

OTHER PUBLICATIONS

Non-Final Office Action for U.S. Appl. No. 12/953,754 dated Oct. 20, 2011.

(Continued)

*Primary Examiner* — Michael K Collins
(74) *Attorney, Agent, or Firm* — Jenkins, Wilson, Taylor & Hunt, P.A.

(57) ABSTRACT

Systems for controlling the dispensing of medication are provided. The system can include a dispenser device capable of holding and delivering at least one medication. A controller can be operatively connected to the dispenser. The controller can automatically operate the dispenser for movement to a dispensing position at a predetermined time. An electronic communication device for connecting the system to a remote facility can be provided. An identification verification device for restricting access to the system can be in communication with the controller of the system. A location determination device for determining the location of the system can also be provided.

20 Claims, 24 Drawing Sheets

(56) References Cited

U.S. PATENT DOCUMENTS

| | | | |
|---|---|---|---|
| RE35,743 E | 3/1998 | Pearson | |
| 5,745,366 A | 4/1998 | Higham et al. | |
| 5,905,653 A | 5/1999 | Higham et al. | |
| 5,971,594 A | 10/1999 | Sahai et al. | |
| 5,993,046 A | 11/1999 | McGrady | |
| 6,011,999 A | 1/2000 | Holmes | |
| 6,332,100 B1 | 12/2001 | Sahai et al. | |
| 6,431,399 B2 | 8/2002 | Gabel et al. | |
| 6,471,087 B1 * | 10/2002 | Shusterman | 221/2 |
| 6,510,962 B1 | 1/2003 | Lim | |
| 6,594,549 B2 | 7/2003 | Spiegel | |
| 6,607,094 B2 * | 8/2003 | MacDonald | 221/121 |
| 6,650,964 B2 | 11/2003 | Spano, Jr. et al. | |
| 6,732,884 B2 * | 5/2004 | Topliffe et al. | 221/3 |
| 6,736,286 B2 | 5/2004 | Hashimoto et al. | |
| 6,961,285 B2 | 11/2005 | Niemiec et al. | |
| 6,962,274 B1 | 11/2005 | Sherman | |
| 7,080,755 B2 * | 7/2006 | Handfield et al. | 221/13 |
| 7,097,068 B2 | 8/2006 | Limback et al. | |
| 7,139,639 B2 | 11/2006 | Broussard et al. | |
| 7,418,311 B1 | 8/2008 | Lagassey et al. | |
| 7,502,664 B2 * | 3/2009 | Berg | 700/236 |
| 7,587,259 B2 * | 9/2009 | Berg | 700/236 |
| 7,753,229 B2 * | 7/2010 | Hutchinson et al. | 221/7 |
| 7,831,336 B2 * | 11/2010 | Gumpert | 700/244 |
| 7,885,725 B2 * | 2/2011 | Dunn | 700/237 |
| 7,886,931 B2 * | 2/2011 | Handfield et al. | 221/154 |
| 8,032,252 B2 | 10/2011 | Berg | |
| 8,326,455 B2 * | 12/2012 | Dunn | 700/237 |
| 8,636,172 B2 | 1/2014 | Dunn | |
| 2007/0156282 A1 | 7/2007 | Dunn | |
| 2009/0308884 A1 | 12/2009 | Coughlin et al. | |
| 2011/0125317 A1 | 5/2011 | Dunn | |
| 2011/0166700 A1 | 7/2011 | Dunn | |
| 2013/0166066 A1 | 6/2013 | Dunn | |

OTHER PUBLICATIONS

Notice of Allowance and Fees for U.S. Appl. No. 12/953,754 dated Aug. 13, 2012.

Non-Final Office Action for U.S. Appl. No. 13/022,354 dated Dec. 17, 2012.

Interactive Medical Developments, L.C., "MD.2 Users Manual", Dec. 1, 2005.

International Search Report and Written Opinion for Application Serial No. PCT/US2012/024118 dated Aug. 24, 2012.

"Monitored Automatic Medication Dispenser MD.2 from e-pill," http://www.age-in-place.com/md2.html (Downloaded from the internet on Nov. 17, 2005).

"e-pill Multi-Alarm: Easy-to-Program Medication Reminder," http://www.age-in-Place.com/multialarm.html (Downloaded from the internet on Nov. 17, 2005).

"Automatic Pill Dispenser: e-pill Med-Time 'Electronic Pill Box' Automatic Medication Dispenser & Reminder," http://www.age-in-place.com/medtime.html (Downloaded from the internet on Nov. 17, 2005).

"MD.2 Personal Medication System," Interactive Medical Developments, L.C., http://www.imd2.com (Downloaded from the internet on Nov. 17, 2005).

"Pyxis Corporation's Positive ID Assures Secure Access to Medications,"Cardinal Health,http://www.cardinal.com/content/news/060198_65988.asp (Downloaded from the internet on Nov. 17, 2005).

"Hendricks Regional Health Adds State-of-theArt Medication-Use Technology to Increase Patient Safety," Omnicell, http://www.omnicell.com/news_events/release_display.asp?page=238 (Downloaded from the internet on Nov. 17, 2005).

"Fingerprint Sensors Enhance Accuracy in User-Authentication Application," Medical Devicelink, http://www.devicelink.com/emdm/archive/03/11/006.html (Downloaded from the internet on Nov. 18, 2005).

"Authentec: The Power of Touch—Electronic Fingerprint Sensor," Authentec main website, http://www.authentec.com (downloaded from the internet on Nov. 18, 2005).

Brian Robinson, "VA Improves Telehealth Access: Slimmer Equipment, Web Access Make a Better Case for Home Care," Technology Briefing (Jan. 6, 2002).

e-pill® website pages, http://www.epill.com/ (downloaded from the internet between Apr. 24, 2012 and May 1, 2012).

MedMinder™ website pages, http://www.medminder.com/ (downloaded from the internet on Apr. 13, 2012).

MedSignals website pages, http://www.medsignals.com/ (downloaded from the internet on Apr. 24, 2012).

TabSafe website pages, http://www.tabsafe.com/ (downloaded from the internet on Apr. 24, 2012).

Vitality™ wesite pages, http://www.vitality.net/index.html (downloaded from the internet on Apr. 13, 2012).

e-pill® product materials and brochures, (downloaded from the internet on May 1, 2012).

MedCenter™ "Recording your Minder, The Talking Personal Recording Alarm Clock", (downloaded from the internet on May 1, 2012).

Timex Healthcare Medication Manager Instruction Manual, (downloaded from the internet on May 1, 2012).

CASIO® User's Guide TMR-200, (downloaded from the internet on May 1, 2012).

Notification Concerning Availability of the Publication Serial No. PCT/US2012/024118 dated Aug. 16, 2012.

Non-Final Office Action for U.S. Appl. No. 11/649,471 dated Nov. 30, 2009.

Final Office Action for U.S. Appl. No. 11/649,471 dated May 19, 2010.

Notice of Allowance for U.S. Appl. No. 11/649,471 dated Sep. 30, 2010.

Notice of Allowance for U.S. Appl. No. 12/953,754 dated Apr. 30, 2012.

Notice of Allowance for U.S. Appl. No. 13/022,354 dated Apr. 23, 2013.

Non-Final Office Action for U.S. Appl. No. 13/691,149 dated May 1, 2013.

Notice of Allowance for U.S. Appl. No. 13/022,354 dated Sep. 24, 2013.

Final Office Action for U.S. Appl. No. 13/691,149 dated Dec. 19, 2013.

Non-Final Office Action for U.S. Appl. No. 13/691,149 dated Jun. 27, 2014.

* cited by examiner

| _rowid | CLINICI | FIRST_NAME | LAST_NAME | PATIENT_ID |
|---|---|---|---|---|
| 2 | 4 | Ross | Simmons | |
| 3 | 2 | Peter | Parker | |
| 5 | 5 | William | Osler | |
| 6 | 6 | Paul | Oddom | |
| 7 | 7 | Alphonse | Kildare | |
| 9 | 9 | Parker | Peter | |

| _rowid | CLINICI | FIRST_NAME | LAST_NAME | PATIENT ID |
|---|---|---|---|---|
| 1 | 1 | Karl | Richter | 1 |
| 2 | 1 | Donn | Smith | 3 |
| 3 | 1 | Peter | Omalley | 2 |
| 4 | 2 | Chelsea | Morn | 4 |
| 5 | 2 | Susan | Ormond | 5 |
| 6 | 2 | Renee | Tolefson | 6 |
| 8 | 3 | Ruth | Morgan | 8 |
| 18 | 4 | Willy | Wonka | 18 |
| 19 | 4 | Henry | Higgins | 19 |
| 20 | 4 | Ricky | Martin | 20 |
| 21 | 4 | Mary | Decker | 21 |
| 22 | 5 | Patty | Duke | 22 |
| 23 | 1 | K's first | patient | 23 |

Dose Tracker Direct:

Providing safety, compliance, and continuity for pharmacotherapy.

Username: _____
Password: _____
Assistant: ☐

[ Login ]

FIG.14

Dose Tracker Direct:

Providing safety, compliance, and continuity for medication.

Entities:

[Clinician ⇕]

[Search...]

[New...]

———

[Home]

[Logout]

Find
Entities:

| Clinician | where [lastName ⇕] is [= ⇕] [_____] 🔍 |
| Patient | where [lastName ⇕] is [= ⇕] [_____] 🔍 |
| Script | where [medication ⇕] is [= ⇕] [_____] 🔍 |
| Tracker | where [trackerNumber ⇕] is [= ⇕] [_____] 🔍 |

FIG.15

Dose Tracker Direct:

Providing safety, compliance, and continuity for medication.

Entities:
[Clinician ⬍]
[Search...]
[New...]

[Home]
[Logout]

List
6 Clinicians

| | First Name | Last Name | Patient ID | |
|---|---|---|---|---|
| ✎ | Alphonse | Kildare | | 🗑 |
| ✎ | Parker | Peter | | 🗑 |
| ✎ | Paul | Oddom | | 🗑 |
| ✎ | Peter | Parker | | 🗑 |
| ✎ | Ross | Simmons | | 🗑 |
| ✎ | William | Osler | | 🗑 |

[ Return ]

FIG.16

Dose Tracker Direct:

Providing safety, compliance, and continuity for medication.

Entities:
[Clinician ⬍]
[Search...]
[New...]

[Home]
[Logout]

Edit
Clinician

First Name [Alphonse]
Last Name [Kildare]
Patient ID [ ]
Patient [7, Zhivago, Yuri
7, Martin, Cecil
7, Najinsky, Dimitri]  ✎

[Cancel] [Delete] [Save]

FIG.17

Dose Tracker Direct:
Providing safety, compliance, and continuity for medication.
| Entities: | List | | | | |
|---|---|---|---|---|---|
| [Patient ⇅] | 32 Patients | Display [10] items | | ◀ Page [1] of 4 ▶ | |
| [Search...] | | | | | |
| [New...] | | First Name ≡ | Last Name ≡ | | |
| |  | | |  | |
| [Home] |  | | |  | |
| [Logout] |  | | |  | |
| |  | | |  | |
| |  | Adrian | Andover |  | |
| |  | Cecil | Martin |  | |
| |  | Chelsea | Morn |  | |
| |  | Cindy | Felen |  | |
| |  | Dimitri | Nojinsky |  | |
| |  | Donn | Smith |  | |
[Return]
FIG.18

Dose Tracker Direct:

Providing safety, compliance, and continuity for medication.

Entities:
[Patient ⇵]     Edit
[Search...]     Patient
[New...]            Clinician  Olser, William ✎
                    First Name [Adrian]
                    Last Name [Andover]
[Home]                 Tracker  <com.webobjects.eocontrol.EOGenericRecord_ed053a_EOIntegral ✎
[Logout]

[Cancel] [Delete] [Save]

FIG.19

Dose Tracker Direct:

Providing safety, compliance, and continuity for medication.

Entities:         List
[Script ⇵]        3 Scripts
[Search...]
[New...]                 Days                                              Tracker
                        LENGTH ≡  Dose ≡  Interval ≡  Medication ≡  Strength ≡  ID ≡
                    ✎    14        1        12         Oxycontin     20          2     🗑
[Home]              ✎    30        2         4         Oxycontin     40          1     🗑
[Logout]            ✎    30        1        24         Avinza       100          3     🗑

[Return]

FIG.20

Dose Tracker Direct:

Providing safety, compliance, and continuity for medication.

Entities:

[Script ⇕]      Edit
[Search...]     Script
[New...]                    Days Length [14]
                                   Dose [1]
                               Interval [12]
[Home]                     Medication [Oxycontin]
[Logout]                      Strength [20]
                             Tracker ID [2]
                                    [Cancel] [Delete] [Save]

FIG.21

Dose Tracker Direct:

Providing safety, compliance, and continuity for medication.

Entities: Tracker

[Search...]
[New...]

[Home]
[Logout]

List
3 Trackers

| | Contact Time | Latitude | Longitude | Patient ID | Pills Remaining | Postition Time | Script ID | Tracker Number | | | |
|---|---|---|---|---|---|---|---|---|---|---|---|
| ✎ | Feb 12,2005 | 234231 | 170334 | 1 | 17 | Feb 12,2005 | 1 | 1 | ▥ | ▥ | ▥ |
| ✎ | Feb 12,2005 | 273453 | 340713 | 2 | 34 | Feb 12,2005 | 2 | 2 | | | |
| ✎ | Feb 12,2005 | 1123421 | 341256 | 3 | 87 | Feb 12,2005 | 3 | 3 | | | |

[Return]

FIG.22

Dose Tracker Direct:

Providing safety, compliance, and continuity for medication.

Entities:

[Tracker ⇅]    Edit
[Search...]    Tracker
[New...]           Contact Time [Feb 12,2005]   *Format: Apr DD, YYYY*
                       Latitude [234231]
[Home]              Longitude [170334]
                       Patient ID [1]
[Logout]          Pills Remaining [17]
                     Position Time [Feb 12,2005]   *Format: Apr DD, YYYY*
                           Script 1, 30, 4, 2, 40, Oxycontin 
                        Script ID [1]
                   Tracker Number [1]

[Cancel] [Delete] [Save]

SYSTEMS FOR POINT-OF-USE MEDICATION CONTROL

RELATED APPLICATION

This application is a divisional of and claims priority benefit to U.S. patent application Ser. No. 11/649,471 filed Jan. 4, 2007, now U.S. Pat. No. 7,885,725 which claims the benefit of U.S. Provisional patent application Ser. No. 60/756,372, filed Jan. 5, 2006, the entire contents of which are both hereby incorporated by reference herein.

TECHNICAL FIELD

The subject matter described herein relates generally to systems and methods for medication compliance. More particular, the subject matter disclosed herein relates to devices, systems and methods for dispensing medication to an intended patient at predetermined and appropriate times in an outpatient setting to increase the likelihood of proper medication management of a patient after leaving the direct care of a doctor or health provider/professional.

BACKGROUND

The rate of compliance with medication regimens in outpatient settings is generally regarded as poor. Even under the watchful eye of doctors, studies have shown that trained professionals working in a controlled setting make significant errors in the delivery of medication to patients. Compliance with such medication regimens have been shown to be worse after the patient leaves the hospital and the medication management is required to be performed by the patient or some other untrained family member. For example, studies have shown that patients directed to take a single medication once per day have only succeeded about 70% of the time. Studies have further shown that, when three doses per day are required, compliance with such medication regimens falls to about 50%. Further, such studies show that compliance and compliance failures for such medication regimens do not correlate with social, economic, or educational variables.

Failure to comply with medication regimens prescribed by doctors can have severe consequences. For example, in the outpatient setting, a patient's recovery can be slowed and progress toward recovery can be minimized by the patient's failure to follow the prescribed medication regimen provided by a trained professional. Such lack of compliance can help in the development of drug resistant strains of bacteria and viruses. For example, tuberculosis has developed certain drug resistant strains in Africa due to the fact that rural patients have begun lengthy medication regimens that required multiple doses but fail to follow through and complete these regimens. Thereby, the tuberculosis has been allowed to persist in a form that has become resistant to the treatment being used. Such drug resistance strains could be minimized if the patients were able to properly follow through with their medication regimens.

A further concern applies to certain classes of medication that are prone to abuse. For example, certain narcotics and anxiety reducing medications are known to be addictive. For such medications, a patient will often begin to take increasing amounts of the medication at more frequent intervals that do not comply with the prescribed regimen set forth for the use of the drug. The controlling of dosing for these medications in the outpatient setting is so notoriously difficult that many physicians have simply begun to refuse to prescribe them.

Concerns about the diversion of a medication from the patient to other individuals have reduced the outpatient prescription of such drugs. For example, medications such as Oxycontin have addictive qualities and also have street value as a recreational drug. Often, people who are prescribed such a drug end up selling it to users who consume it recreationally. This concern is so great for Oxycontin that some state legislatures have considered banning its use.

In the examples provided above, drugs that were once valuable to society have lost part of their effectiveness through their misuse in one way or another. Therefore, in light of the above, a need exists for a system that allows outpatient medication to be dispensed in a secured, controlled, and monitored fashion to more effectively manage and organize the care given to a patient.

SUMMARY

In accordance with this disclosure, novel devices, systems and methods for point-of-use medication control in outpatient settings are provided.

The present disclosure provides devices, systems and methods for point-of-use medication control that can employ single dose distribution and dispensing at predetermined and appropriate times through patient awareness and identification as well as through compliance confirmation. This and other purposes as may become apparent from the present disclosure can be achieved, in whole or in part, by the presently disclosed subject matter when taken in connection with the accompanying drawings as best described herein below.

BRIEF DESCRIPTION OF THE DRAWINGS

A full and enabling disclosure of the present subject matter including the best mode thereof to one of ordinary skill in the art is set forth more particularly in the remainder of the specification, including references to the accompanying Figures in which:

FIG. 9 illustrates a screen of a database that employs the data tables of FIG. 6;

FIG. 10 illustrates a screen of a database that employs the data tables of FIG. 6;

FIG. 11 illustrates a screen of a database that employs the data tables of FIG. 6;

FIG. 12 illustrates a screen of a database that employs the data tables of FIG. 6;

FIG. 14 illustrates an interactive screen display window used for an internet web browser interface for a database of an embodiment of a system for a point-of-use medication control according to the present subject matter;

FIG. 15 illustrates an interactive screen display window used for an internet web browser interface for a database of an embodiment of a system for a point-of-use medication control according to the present subject matter;

FIG. 16 illustrates an interactive screen display window used for an internet web browser interface for a database of an embodiment of a system for a point-of-use medication control according to the present subject matter;

FIG. 17 illustrates an interactive screen display window used for an internet web browser interface for a database of an embodiment of a system for a point-of-use medication control according to the present subject matter;

FIG. 18 illustrates an interactive screen display window used for an internet web browser interface for a database of an embodiment of a system for a point-of-use medication control according to the present subject matter;

FIG. 19 illustrates an interactive screen display window used for an internet web browser interface for a database of an embodiment of a system for a point-of-use medication control according to the present subject matter;

FIG. 20 illustrates an interactive screen display window used for an internet web browser interface for a database of an embodiment of a system for a point-of-use medication control according to the present subject matter;

FIG. 21 illustrates an interactive screen display window used for an internet web browser interface for a database of an embodiment of a system for a point-of-use medication control according to the present subject matter;

FIG. 22 illustrates an interactive screen display window used for an internet web browser interface for a database of an embodiment of a system for a point-of-use medication control according to the present subject matter.

DETAILED DESCRIPTION

Reference will now be made in detail to presently preferred embodiments of the present subject matter, one or more examples of which are shown in the Figures. Each example is provided to explain the subject matter and not as a limitation. In fact, features illustrated or described as part of one embodiment can be used in another embodiment to yield still another embodiment. It is intended that the present subject matter cover such modifications and variations.

Figure 1:
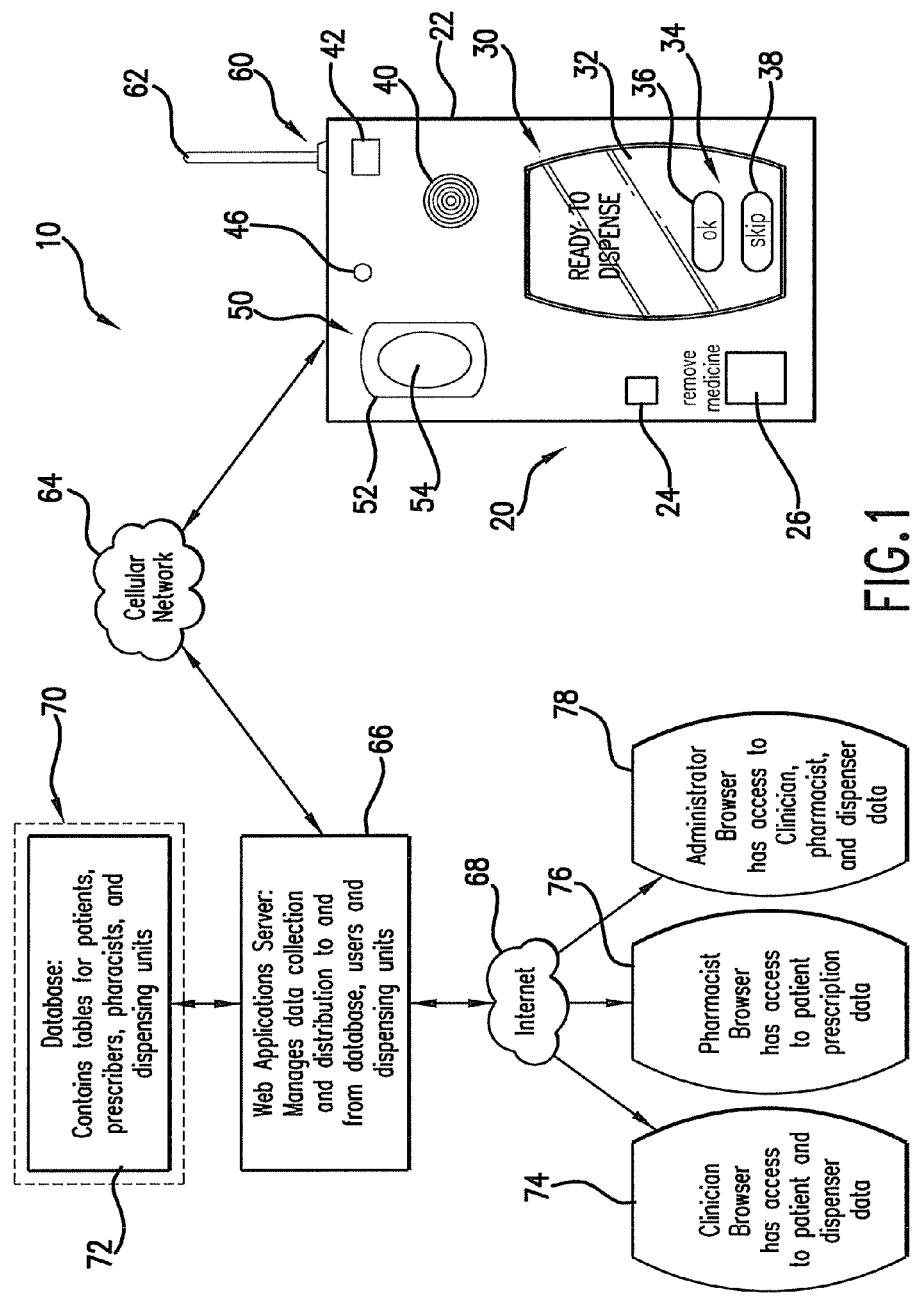
FIG. 1 illustrates a schematic of an embodiment of a system for a point-of-use medication control according to the present subject matter.

FIG. 1 illustrates a medication dispensation control system, generally designated as 10. System 10 includes a dispenser, generally designated as 20, that is capable of holding and delivering at least one dose of medication to a patient in an outpatient setting. Dispenser 20 can have an outer housing 22 that encloses the operational components of a portion of system 10 within dispenser 20 and prevents tampering and unauthorized removal of medication from dispenser 20. In use, dispenser 20 could be used to distribute units of medications in the form of tablets, pills or capsules at predetermined times to specified and identified individuals.

System 10 can also include a controller, generally designated as 30. Dispenser housing 22 can enclose controller 30, which is operably connected to operable components of dispenser 20. Controller 30 can automatically operate dispenser 20 to provide a dose of medication to the patient at the appropriate or predetermined time. For example, controller 30 can be programmable with a medication dispensing program which includes a data store comprising the predetermined time to operate dispenser 20 and the name of the at least one medication. The data store of the medication dispensing program can also comprise patient data and a patient compliance schedule. Patient data can include the first and last name of the patient, the age of the patient, medical history information, or the like. Biometric information, such as fingerprint data or the like can also be considered patient data.

The data store of the medication dispensing program on controller 30 can also comprise caregiver data. The caregiver can be anyone such as a family member or nurse who is charged with taking care of the patient. In such cases where a caregiver is necessary to administer the medication to the patient, the caregiver can be allowed to engage system 10 to receive the medication to be administered to the patient. Caregiver data can include first and last name of the caregiver, contact information of the caregiver, or the like. Biometric information, such as fingerprint data or the like can also be considered caregiver data. Through such information, the caregiver can gain access to the medication to be administered to the patient.

The data store of the medication dispensing program on controller 30 can also comprise compliance notification data. Compliance notification data can include the frequency of timely compliance by the patient, data on the dates and times at which compliance occurs, or the like. The data store of the medication dispensing program on controller 30 can further comprise pharmacy data, physician data, insurance data and emergency contact data.

Controller 30 can include devices that emit any suitable type of signal to indicate dispenser 20 is ready to provide a dose of medication for the patient to receive. For example, a display screen, such as an interactive user interface display screen 32 can be provided that can alert the patient that a dose of medication is ready to be dispensed. In the embodiment shown in FIG. 1, a simple display saying that the dispenser is ready to dispense is shown on display screen 32. The display also shows a user interface 34 on display screen 32 with which the patient can interact to acknowledge receipt of the signal. The user interface 34 can be a response button 36 in the form of a graphic display button that the user activates by touching the screen at the display location of the graphic display button. By activating this button 36, the patient acknowledges receipt of the signal and the dispensing can begin. Other response mechanisms can be provided including other graphic display buttons. For example, button 38 can be provided that allows the patient to skip the dispensing of the dose of medication.

Besides the display 32, a speaker 40 can be provided to provide an audible signal that would be emitted by the speaker 40. Speaker 40 can be internally contained with outer housing 22 or it can be external. In this manner, a patient who cannot view display 32 can still be notified of the availability of the dose medication. Once the patient has acknowledged receipt then the audible signal can end as well. Other response mechanisms can be provided to allow the user to acknowledge receipt of the signal that medication is available for dispensing. For example, a physical button can be provided that the patient can activate. Further, a lever or switch can be provided that can be activated by the patient after receipt of the signal.

To monitor and verify that the dispensing of the drug is to the correct individual, an identification verification device, generally designated as 50, can be provided in outer housing 22 of dispenser 20 and can be connected to controller 30. Identification verification device 50 can be used to verify that the patient for whom the medication is to be given is present and ready for distribution of the medication. In this manner, identification verification device 50 can be used to verify the identity of the patient.

The identification verification device 50 can be a biometric identification device. For example, TruePrint technology based fingerprint sensors offered by AuthenTec, Inc. of Melbourne, Fla., can be used as the fingerprint system 52. Fingerprint system 52 can include a touch screen 54 that can provide a place for the patient to place a finger. Fingerprint system 52 can then read the fingerprint and compare it to stored data to confirm that the individual trying to receive the doses of medication is in fact the intended recipient.

Other identification verification devices such as retina scans, user passwords, voice recognition or the like can be used to verify the identity of the patient before distribution of the dose of medication within dispenser 20.

System 10 can further include a communication device 60 that can also be in operable communication with controller 30. Communication device 60 can be a wireless communication device. Such an electronic communication device 60 that operate on a wireless platform and can include an antenna 62 that transmits signals through a cellular network 64 to a remote facility, or location 70 that can house a database 72 for use in controlling dispenser 20. Database 72 can be accessed by the patient's doctor, pharmacy, and/or administrator of the medication system, as well as the patient. Through the wireless connection provided by cellular network 64, controller 30 can communicate through an Internet Service Provider 66 with the database 72 at the remote facility 70. Internet Service Provider 66 manages data collection and distribution to and from database 72 for the users. The users can include the patient, the patient's doctor and/or pharmacist, and/or the administrator of the medication system.

Through the Internet 68, appropriate individuals can gain access to the information provided to and from dispenser 20 to monitor and control the dosing of the medication. For example, such individuals or locations can include the patient, the doctor's office, the pharmacy, or the administration facility, where administrator resides. Authorized personnel from the doctor's office can gain access to patient and dispenser information stored on database 72 through a clinician browser 74. Authorized personnel from the pharmacy can gain access to patient prescription information stored on database 72 through a pharmacist browser 76. Authorized personnel from the administration facility can gain access to clinician, pharmacist, and dispenser information stored on database 72 through an administrator browser 78. Data stored can include information such as predetermined times to operate dispenser 20. The data can also include the name of the medication being distributed, the patient's data, the patient's compliance schedule, caregiver data, and compliance notification data as well as pharmacy data, physician data, insurance data, and emergency contact data. Further, such information can be provided on a data store connected to controller 30 within dispenser 20 itself.

Controller 30 is programmable to connect to a predetermined Internet Service Provider 66 through electronic communication device 60 and cellular network 64 in order to transmit the patient's data and obtain a patient registration. Controller 30 can also be programmable to connect to Internet Service Provider 66 through electronic communication device 60 in order to transmit the compliance schedule and compliance notification data from database 72. Controller 30 can also be programmable to connect to Internet Service Provider 66 through communication device 60 in order to transmit or receive the pharmacy data, physician data, insurance data, and emergency contact data.

When controller 30 has received instruction that the signal has been received, controller 30 can transmit a compliance notification to Internet Service Provider 66 to be sent on to the physician, pharmacist, or administrator. Alternatively, the compliance notification can be sent to database 72 where the physician, pharmacist or administrator can access the notice of compliance. Similarly, if the recipient does not acknowledge the signal and the signal goes on for a predetermined time, controller 30 can send a signal to Internet Service Provider 66 to transmit a non-compliance notification that then can be forwarded onto the physician, pharmacist, or administrator as well as stored in the database as needed.

The user can use display screen 32 to communicate with controller 30 to order a refill of the medication or to order a new dispenser 20 containing the medication when the system is connected to the predetermined Internet Service Provider 66. In this manner, the user can take dispenser 20 back to the pharmacy to have it refilled or to pick up a new dispenser 20 which can be taken back and used by the patient. The interchangeable dispensers 20 provide a way to easily monitor the drugs that are placed into each dispenser 20 by the pharmacist. The pharmacist can ensure that the correct information is downloaded into controller 30 within the appropriate dispenser 20 for the appropriate patient before the patient picks that dispenser 20 up from the pharmacy or doctor's office.

Controller 30 can also be programmable to update and transmit the caregiver data and compliance notification data to the database or Internet Service Provider 66 and/or the clinician browser 74, pharmacist browser 76, or administrator browser 78 when the system is connected to Internet Service Provider 66. Controller 30 can automatically connect and send such information as needed or desired. Further, communication device 60 can receive notices from the predetermined Internet Service Provider 66 when the system is connected to the predetermined Internet Service Provider 66. Controller 30 can be programmable to receive and use notices as necessary to better manage dispenser 20. Similarly, controller 30 can be programmable to access and search databases provided by Internet Service Provider 66.

System 10 can also include a location determination device (not specifically shown) such as an integrated global positioning system ("GPS") receiver that can be contained within outer housing 22 of dispenser 20. For example, a location determination device can be integrated into controller 30. Such a device permits the whereabouts of dispenser 20 to be easily determined. If someone tries to steal dispenser 20 or dispenser 20 is misplaced, the patient can contact the administrator who can track down the location of dispenser 20. For example, the administrator can use tracking software and communication systems of a GPS system used within dispenser 20 for determining the location of that dispenser 20. In this manner, theft of the dispenser can be minimized, and, hopefully, the chances of the perpetrator being caught and prosecuted can be increased.

System 10 can also include a telephone modem within dispenser 20 that allows it to be hooked up to a telephone line to call for emergency assistance, if needed. Dispenser 20 can include an emergency assistance button 24 that can be actuated to cause controller 30 to dial an emergency telephone number. Dispenser 20 can also include a dispensing door 26 which can be used to permit access into dispenser 20 to remove a dose of medication. Dispenser 20 can also include a microphone 42 to allow for the patient to communicate with an emergency facility, which is contacted by controller 30.

Dispenser 20 can further include a lockout for disabling functionality of the system based upon predetermined criteria. Such a lockout can be in furtherance to identification verification device 50, which can also be used to prevent unwanted access to the medication contained in dispenser 20. However, the lockout can help to prevent overdosing of the patient or dosing of the patient when the patient is not in a condition to receive such medication. For example, the lockout can include a breath sensor 46 for determining a breath alcohol level. The breath alcohol level can then be compared to predetermined criteria that can include a maximum breath alcohol level that would be allowable for dispensing of the dose of medication from dispenser 20. The lockout can also include an interactive cognitive test on predetermined criteria that can include a minimum cognitive level based on the results of the test to allow dispensation of the dose of medication from dispenser 20. The interactive cognitive test can be performed through a display on the interactive display screen 32. In this manner, overdosing can be prevented as well as dosing of a patient who is too heavily medicated or disoriented to take the medication. Health hazards relating to the mixing of medications or alcohol with medications can be prevented. Based on the results from the lockout, an emergency contact, the doctor's office, pharmacy or a caregiver of the patient can be alerted that the patient is in a state that requires attention.

Figure 2:
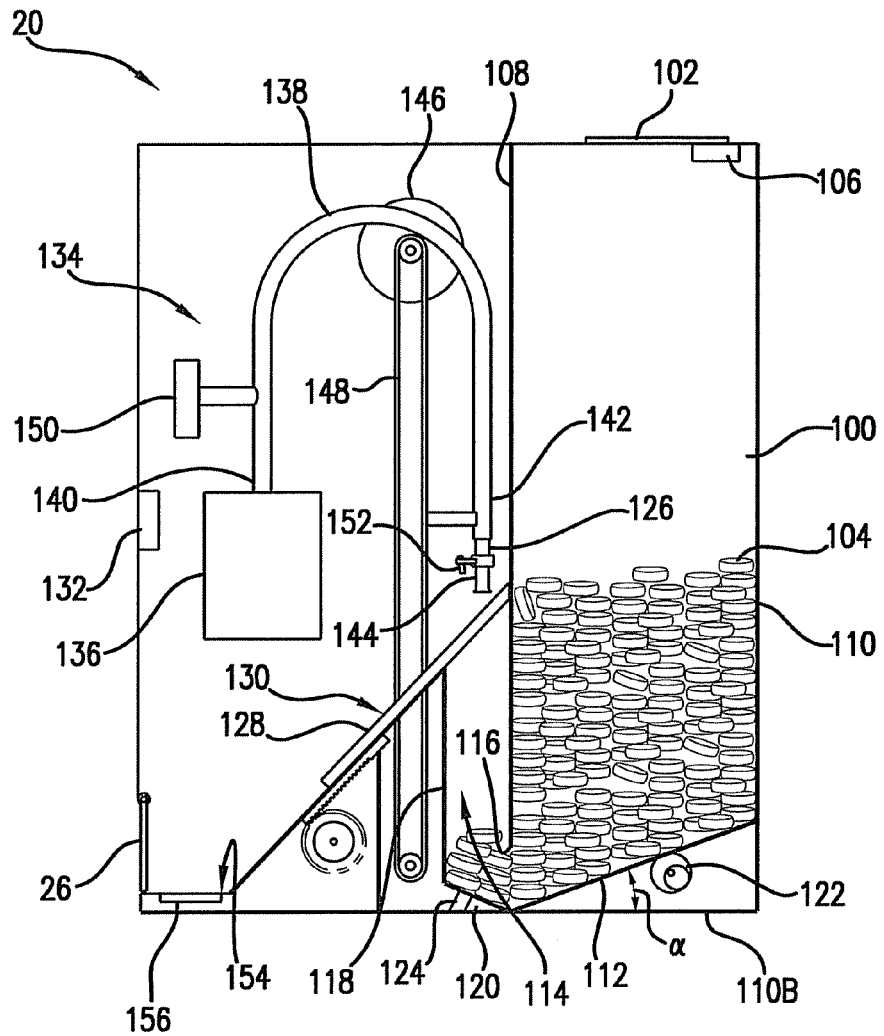
FIG. 2 illustrates a schematic of an embodiment of a dispenser device used within the system according to FIG. 1.

FIG. 2 illustrates a schematic internal view of the dispenser 20. Dispenser 20 includes a pill magazine 100 which can be filled at a pharmacy through a fill door 102. Fill door 102 can be locked to prevent access to the store of pills 104 within pill magazine 100. A tamper switch 106 can also be provided to monitor and record the opening of fill door 102 or other tampering that can occur to fill door 102 once dispenser 20 has left the pharmacy.

Pill magazine 100 can be defined by an inner wall 108 and an outer wall 110 and two side walls. Further, a slanting base surface wall 112 can extend within the dispenser 20 from the outer wall 110 downward to a bottom wall 110B forming an angle α with bottom wall 110B. Inner wall 108 does not extend to base surface wall 112, thereby leaving an opening for pills to slide downward into a dispensing well 114.

Outer wall 110 and/or bottom wall 110B can be internal walls that reside within outer housing 22 (shown in FIG. 1). Alternatively, outer wall 110 and/or bottom wall 110B can be external walls which help to form outer housing 22 of dispenser 20.

At a filling location such as a pharmacy, when fill door 102 is opened and pills 104 are placed into pill magazine 100, pills 104 flow downward under gravitational force to the base surface wall 112 and slide down its sloped surface which slopes downward from external wall 110 at angle α. The pills 104 can slide into dispensing well 114 underneath end 116 of inner wall 108. A dispensing well wall 118 extends upward and parallel to inner wall 108 of pill magazine 100 to help define an opening in dispensing well 114. Dispensing well wall 118 permits only a small number of the pills from pill magazine 100 fill the dispensing well 114 at any given time.

Dispensing well wall 118 can also include a slanted base wall 120 that slopes upward from the base surface wall 112 of pill magazine 100. A vibrator 122 can be used and positioned below base surface wall 112 to add vibration to base surface wall 112, thereby agitating pills residing on base surface wall 112. This vibration can cause pills 104 to fall or move down the sloped surface of the base surface wall into dispensing well 114. Vibrator 122 can be in communication with an optical detector 124 which can be placed along dispensing well wall 118 or base surface wall 120. Optical detector 124 can detect whether any pills reside in dispensing well 114. If optical sensor 124 does not detect the presence of pills 104 within dispensing well 114 then vibrator 122 can be activated to cause any pills residing in pill magazine 100 to slide down the slope surface of base surface wall 112. Optical detector 124 can be any conventional optical sensor known in the art.

Once it is determined that pills 104 reside in dispensing well 114, a vacuum pick up 126 can be actuated to pickup a pill 104 for delivery to dispensing door 26 of dispenser 20. The opening of dispensing well 114 can be opened and closed by motorized shutter 128, which can provide a slanted surface 130. When motorized shutter 128 is in a closed position as shown in FIG. 2, pills 104 within pill magazine 100 and dispensing well 114 are prevented from removal from dispenser 20.

A tilt sensor 132 can be provided which is activated when dispenser 20 is tilted to prevent its operation while inverted or shaken. Tilt sensor 132 can be in communication with controller 30 (see FIG. 1). Such information as whether dispenser 20 is shaken or tilted can be sent from tilt sensor 132 to controller 30. Controller 30 can then render dispenser 20 inoperable and it can also forward a message to Internet Service Provider 66 and onto the clinician browser 74, pharmacist browser 76, or administrator browser 78 (see FIG. 1). Tilt sensor 132 can be a conventional equilibrium sensor. Tilt sensor 132 can also be configured to shut down dispensing operations directly if tilting or shaking is detected.

Dispenser 20 also can include, as noted above, a vacuum pickup 126, which can be a part of a vacuum mechanism 134 for removal of at least one pill from dispensing well 114 for delivery to dispensing door 26 of dispenser 20. Vacuum mechanism 134 can include a vacuum pump 136 that creates a negative pressure that can be used to pick up a pill 104 from dispensing well 114. Vacuum mechanism 134 can also include a vacuum tube 138 that is connected to vacuum pump 136 on one end 140 such that the negative pressure created within vacuum pump 136 creates a vacuum through vacuum tube 138. Vacuum pickup 126 can be secured on the other end 142 of vacuum tube 138. Vacuum pickup 126 as well as vacuum tube 138 can be extended into dispensing well 114 to retrieve a pill therefrom.

Vacuum pickup 126 can include a vacuum cup 144 disposed at its end distal from vacuum tube 138. Vacuum pickup 126 can be raised and lowered by a step motor 146. In the embodiment shown, step motor 146 can rotate a belt 148 which is secured to the vacuum pickup 126. By running step motor 146 in one direction, vacuum pickup 126 is lowered. By running step motor 146 in a reverse direction, the rotation of belt 148 can be reversed and vacuum pickup 126 can be raised.

A vacuum sensor 150 can be in communication with vacuum mechanism 134. Vacuum sensor 150 can detect whether or not a pill is stuck to the vacuum pickup 126 at vacuum cup 144 thereof. In this manner, vacuum mechanism 134 determines when a pill is secured to vacuum pickup 126 so that it can be raised from dispensing well 114 and ready for delivery to dispensing door 26 of dispenser 20.

In operation, once the patient has acknowledged receipt of the signal indicating time for the receipt of a dose of medication and the patient has identified himself or herself to system 10, dispenser 20 is ready to dispense a dose of medication to the intended recipient. When a pill 104 is to be dispensed, motorized shutter 128 can be moved from its closed position as shown in FIG. 2 to an open position (see FIGS. 3A and 3B) to allow vacuum pickup 126 to be lowered into dispensing well 114. As noted above, tilt sensor 132 can prevent shutter 128 from opening if dispenser 20 is tilted, inverted or shaken.

Optical sensor 124 can check to determine if any pills 104 are in position within dispensing well 114 to be picked up by vacuum pickup 126. If no pills 104 have fallen into dispensing well 114, vibrator 122 vibrates base surface wall 112 to agitate base surface wall 112 within pill magazine 100 to cause any pills 104 within pill magazine 100 to fall down the sloped surface of base surface wall 112 into position within dispensing well 114. As noted above, base surface wall 112 can be at an angle α as measured from the bottom outer wall 110B that provides enough of a slope to encourage pills 104 to slide into dispensing well 114.

As vacuum pickup 126 is lowered, vacuum pump 136 creates negative pressure which creates a vacuum suction through vacuum cup 144 of the vacuum pickup 126. As vacuum cup 144 comes in contact with a pill and thereby seizes the pill through vacuum pressure, vacuum sensor 150 detects that a pill is stuck to vacuum pickup 126. Step motor 146 can then be run in reverse, such that vacuum pickup 126 is raised out of dispensing well 114.

Optionally, an optical detector 152 can be secured to vacuum pickup 126 to make sure a pill is in position for pickup. Optical detector 152 optically determines if a pill resides within dispensing well 114 that can be picked up through vacuum pickup 126. If no pill is sensed by the optical detector 152, then vibrator 122 can be run. Vacuum pickup 126 can be lowered by step motor 146 by rotating belt 148 in a specified direction until optical detector 152 detects a pill at the pickup. Vacuum pump 136 starts creating a negative pressure that lifts the pill to vacuum cup 144. Vacuum sensor 150 then detects that a pill is stuck to vacuum pickup 126. If a pill is detected, vacuum pickup 126 is raised by reversing step motor 146 so that belt 148 raises vacuum pickup 126.

Once vacuum pickup 126 with the pill attached to vacuum cup 144 has cleared dispensing well 114, motorized shutter 128 can then be moved into a closed position of the opening in dispensing well 104 as shown in FIG. 2. At this point, the vacuum pump 136 shuts off, allowing the pill to fall against slanted surface 130 of shutter 128. The pill falls to a removal position 154 at dispensing door 26 of dispenser 20. An optical sensor 156 can be placed in proximity to removal position 154 to detect that the pill is in place before allowing access to the pill through dispensing door 26. If no pill is detected, then the steps of picking up a pill through vacuum pickup 126 can be repeated until it is recognized that a pill is in position for removal from dispensing door 26 of dispenser 20. Vacuum pickup 126 can be recessed slightly into the body of dispenser 20 to ensure that the pill attached thereto drops freely when the vacuum is removed.

Figure 3A:
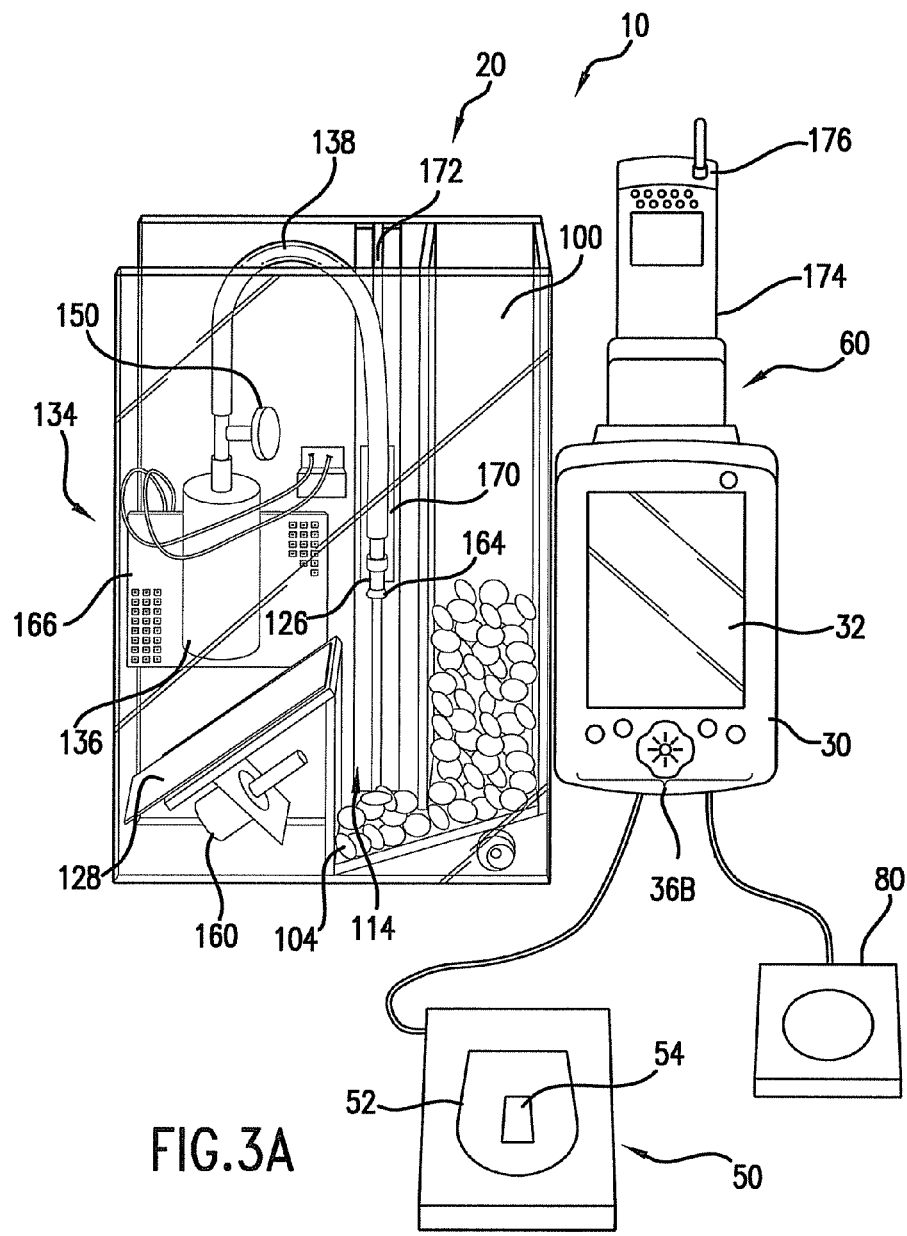
FIGS. 3A-3C illustrate perspective views of components of an embodiment of a system for a point-of-use medication control according to the present subject matter.
Figure 3B:
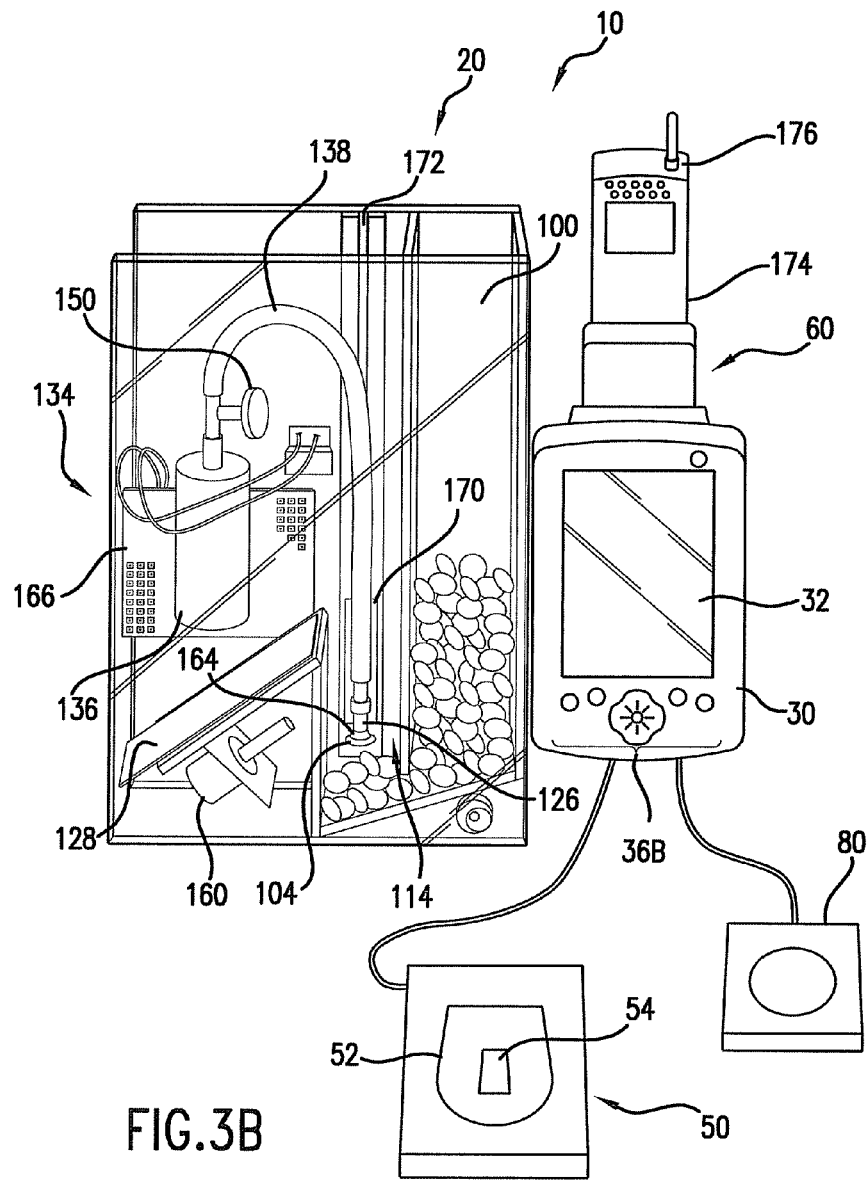
Figure 3C:
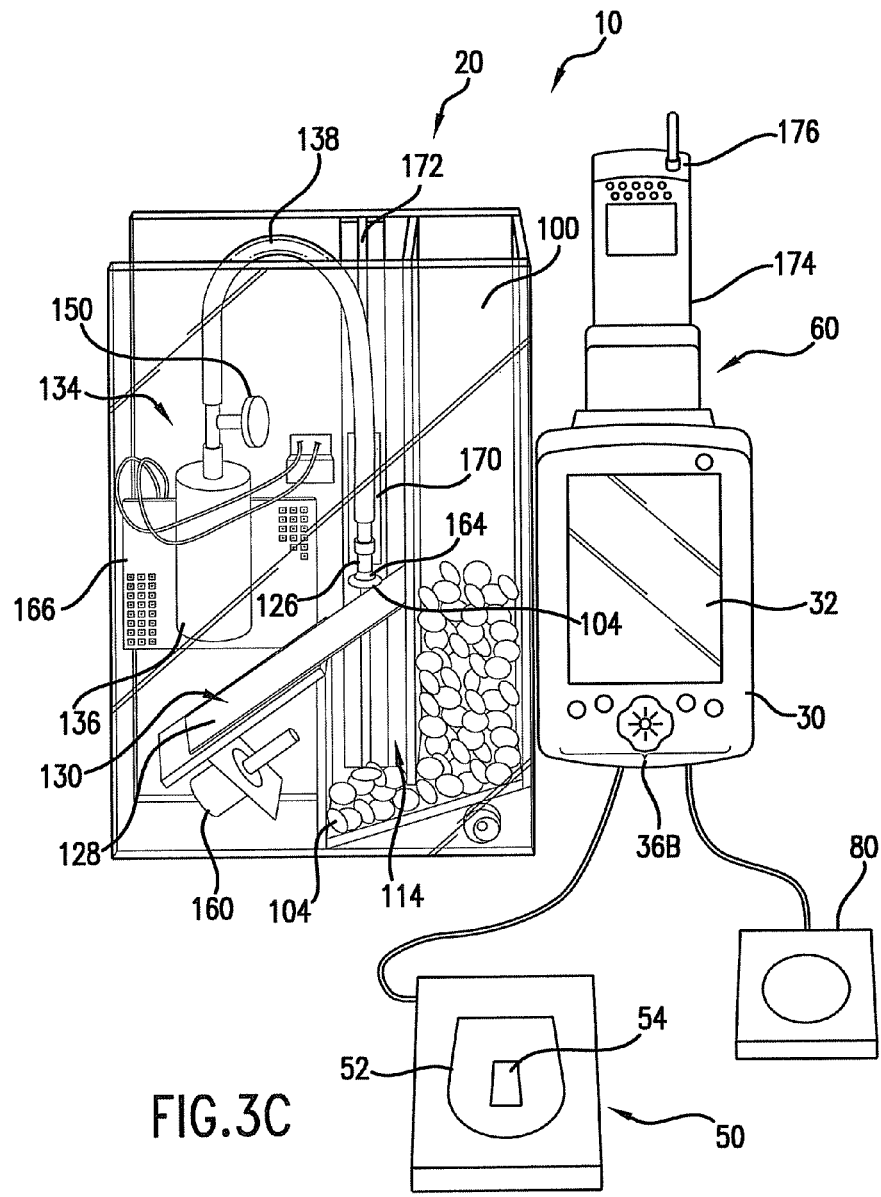

FIGS. 3A, 3B, and 3C illustrate components of an embodiment of a system 10, including a dispenser 20 outside of its outer housing that can be used to enclose the dispenser 20 and the other components. The components are shown free standing relative to one another and can be arranged in any known manner that provides necessary access to any interactive component that the patient must engage to receive the intended doses of medication. Dispenser 20 can include pill magazine 100, vacuum mechanism 134, and motorized shutter 128 as well as dispensing well 114. A controller 30 as well as an identification verification device 50 can also be included as components of system 10. Further, a location determination device 80 can be included in system 10. As noted above, location determination device 80 can be a GPS device that can easily be used to locate the whereabouts of the system 10. Controller 30 can be a microcomputer such as a personalized digital assistant ("PDA"), for example, an Ipaq 3635. Controller 30 can also be a computer, programmable logic controller, or the like. Controller 30 can operate using any compatible operating system. For example, controller 30 can operate using Microsoft Pocket PC. Controller 30 can provide a display screen 32 which can be a touch-tone interactive display. Further, controller 30 can provide physical buttons 36B which control a cursor on display screen 32 to allow interaction between the patient-user and the controller 30.

Controller 30 can be in communication with identification verification device 50 in the embodiment shown. Identification verification device 50 can be a fingerprint reader 52 which has a touch screen 54 on which a patient-user can place a finger in order for the fingerprint reader 52 to read the user's fingerprint.

Controller 30 can also be in communication with the vacuum pump 136 of vacuum mechanism 134 as well as a step motor 160 that is used to control shutter 128 for opening and closing of shutter 128 to provide access through the opening in dispensing well 114. Further, controller 30 can be in communication with step motor 162 (shown in FIG. 4) used to raise and lower vacuum pick up 126 through a slide 170 to which vacuum cup 164 is attached. Slide 170 rides within a slot 172 that extends downward into dispensing well 114. Vacuum sensor 150, which is used to determine the presence of a pill on vacuum pump 164, also can be in communication with controller 30.

Vacuum mechanism 134 components can be controlled by a separate vacuum controller 166 as shown in FIGS. 3A-3C and 4 that is in communication with the controller 30. Such vacuum controller 166 can be a Parallax microcontroller offered by Parallax, Inc., of Rocklin, Calif. Controller 30 can direct operation of vacuum mechanism 134 by communicating with vacuum controller 166. In other embodiments, controller 30 can directly control vacuum mechanism 134 and its components.

Location determination device 80 can be in communication with controller 30 to pass location information to the controller 30 and onto a remote facility 70 or Internet Service Provider 66 (See FIG. 1). Further, location determination device 80 can produce a signal that is independent of controller 30 and communication device 60 that is detectable by an appropriate positioning system such as a GPS. In such embodiments, the signal from the location determination device 80 can be picked up by the administrator as needed.

All components of system 10 can share a common battery power supply (not shown). All components of system 10 can also communicate with controller 30 via an RS232 serial interface.

In operation, controller 30 can be preloaded and programmed with dispensing instructions as to the times of use at the location where dispenser 20 is filled. Programming and fingerprint template transmission also can be done remotely. A patient's fingerprint would only need to be enrolled once for use on multiple units.

Pill magazine 100 of dispenser 20 can store a single type of pill or capsule therein. Pill magazine 100 can be filled at a pharmacy. Dispenser 20 can then be secured to prevent access to pill magazine 100 or prevent unauthorized removal of the pill or capsule from dispenser 20. As described, a fill door (not shown) can be used to fill pill magazine 100. The fill door can then be locked and a tamper switch can be used to detect any opening of the fill door.

Once controller 30 determines it is time to dispense medication to the patient, a signal can be sent out to notify the patient that it is time to receive a dose of medication. For example, a visual signal can be shown on display screen 32 to notify the patient of availability of the dose of medication. Additionally, or alternatively, an audible signal through a speaker system (not shown) can be sent out by controller 30 to alert the patient of the availability of a dose of medication. The patient can acknowledge receipt of the signal through use of buttons 36B. Then, the patient can verify his or her identity through identification verification device 50. The patient can interact with system 10 via display screen 32 of controller 30, or through buttons 36B of controller 30, to verify the cognitive level of the patient through cognitive tests. Additionally, or alternatively, a breath analyzer mechanism can be provided to discern the alcohol level within the bloodstream of the patient to ensure no ill effects of mixing the medication and alcohol will result from allowing dosage to be dispensed to the patient. Once identification has been verified and any cognitive tests which can be employed have been fulfilled, controller 30 can instruct vacuum mechanism 134 to remove a pill or capsule for distribution to the patient.

At such time, step motor 160 can drawn back shutter 128 such that dispensing well 114 is opened to allow vacuum pick up 126 to enter dispensing well 114 to remove a pill or capsule disposed therein as shown in FIG. 3A. As discussed above, a tilt sensor can be disposed within the dispenser that identifies when the machine is titled, inverted, or shaken. In such instances, shutter 128 is placed immediately into a closed position, if it is not already in that position, and dispenser 20 is rendered inoperable. Further, dispenser door 26 can be secured in a shut position to prevent removal of any pills, and controller 30 can send a signal to the appropriate locations to notify doctors, pharmacist, or an administrator of the unauthorized use of dispenser 20.

Figure 4:
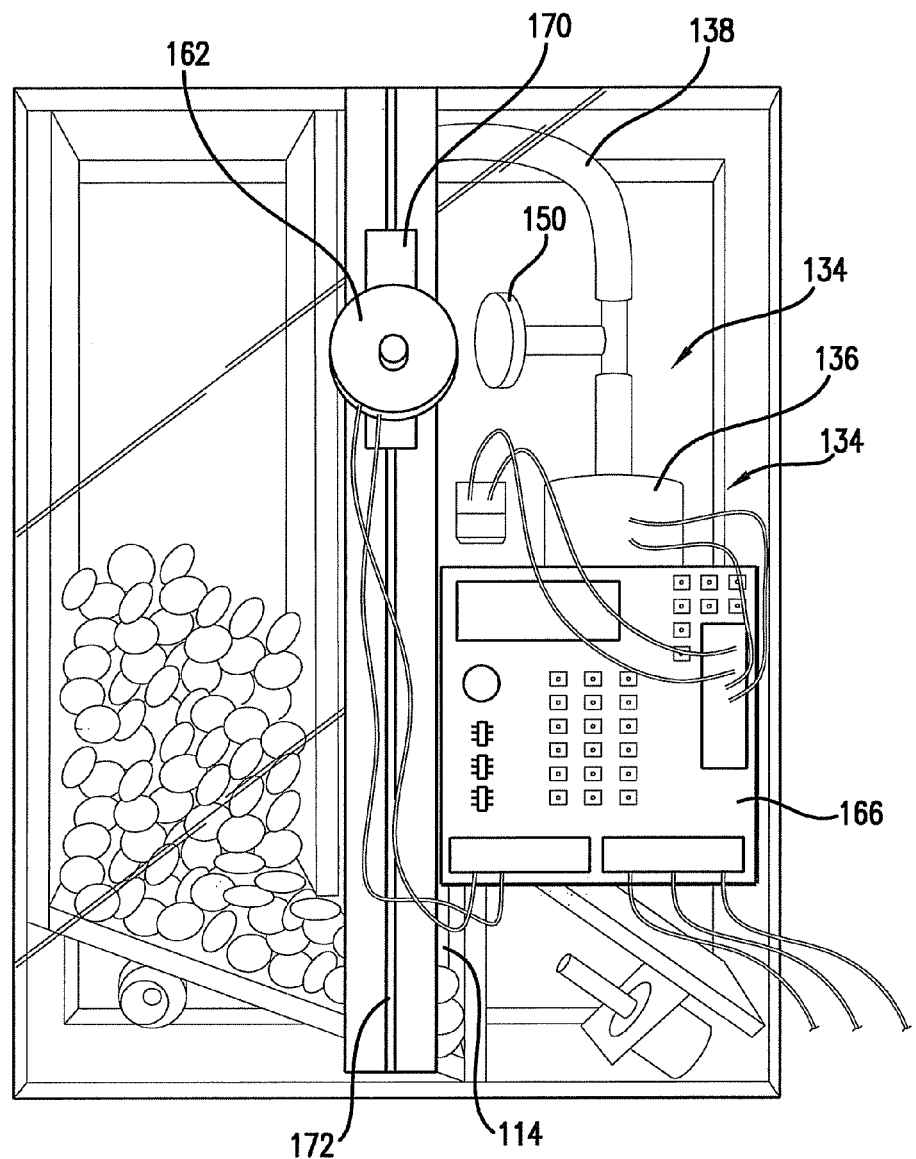
FIG. 4 illustrates a backside perspective view of a component of the embodiment of the system for a point-of-use medication control according to FIGS. 3A-3C.

Once shutter 128 is in an open position as shown in FIG. 3A, vacuum pick up 126 with its vacuum cup 164 can be inserted into the well through the motion of step motor 162. In the embodiment shown in FIG. 4, step motor 162 operates a slide 170 in a conventional manner, so that slide 170 is moveable along a slot 172. For example, slide 170 may be attached to a belt (not shown) that can be rotated in a forward or reverse direction by step motor 162. Slot 172 can run parallel to dispensing well 114 and can extend above dispensing well 114 as shown in FIG. 4. Vacuum pickup 126 (shown in FIGS. 3A-3C) can be secured to slide 170 such that vacuum cup 164 extends downward. Vacuum cup 164 can be a bellow type vacuum cup, which easily secures to a pill or capsule once placed under a negative pressure.

Once shutter 128 is moved to its open position through step motor 160, vacuum pickup is lowered by step motor 162 into dispensing well 114. Controller 30, or alternatively the vacuum controller 166 as shown in FIG. 4, can start vacuum pump 136 to create a negative pressure through vacuum tube 138. This negative pressure creates a vacuum through vacuum cup 164 at the end of vacuum pickup 126. As shown in FIG. 3B, step motor 162 lowers vacuum pickup 126 into dispensing well 114 such that vacuum cup 164 comes in contact with a pill or capsule. The negative pressure created by vacuum pump 136 pulls the pill or capsule against vacuum cup 164 such that the pill or capsule is held by vacuum cup 164 for removal from dispensing well 114. Controller 30, or vacuum controller 166, verify by vacuum sensor 150 that vacuum cup 164 has picked up a pill or capsule. At this point, controller 30, or vacuum controller 166, will then instruct step motor 162 to raise vacuum pickup 126 out of dispensing well 114. Vacuum sensor 150 will continue to monitor to ensure that a pill or capsule is secured by vacuum cup 164. Once the step motor 162 has raised vacuum pickup 126 to a predetermined point above dispensing well 114, controller 30, or vacuum controller 166, will instruct step motor 162 to close shutter 128 as shown in FIG. 3C.

Once vacuum pickup 126 with a pill or capsule attached to vacuum cup 164 is raised above dispensing well 114, shutter 128 can be closed. Controller 30, or vacuum controller 166, can turn off vacuum pump 136. Thereby, the negative pressure is removed from the vacuum pickup 126 and vacuum cup 164 allows the pill or capsule secured thereto to drop onto slanted surface 130 of shutter 128. Slanted surface 130 feeds the pill or capsule into the chute and down to removal position 154 in front of dispenser door 26 as shown in FIG. 2. At this point, the pill or capsule is ready for removal from dispenser 20 by the patient or caregiver.

Once the patient has used a fingerprint touch sensor 52 to confirm identity and the proper number of pills or capsules are dispensed and removed, controller 30 records the removal of the pills. After dispensing medication on timed intervals, controller 30 can activate a cellular modem 174 of a communication device 60 and connect to a computer server to exchange data with the Internet Service Provider server and the database that contains tables for patients, pharmacists and dispensing units. For example, information can be exchanged twice a day. Further, information can be provided to the patient's doctor, pharmacist and the administrator of the out-patient medication system. In this manner, data can be exchanged between controller 30 and the computer which provides access to other necessary parties including the patient through the cellular modem 174 and antennae 176 of the electronic communication device 60, both of which are in communication with controller 30. For example, dose history can be sent to the server in this manner. Further, if the dispenser is reported as lost, the server can communicate with the dispenser, while the location determination device 80 can be used to identify the location of the dispenser. Once the location is determined, coordinates are then relayed to the server so the dispenser can be located and recovered.

Software running on the database server 72 (see FIG. 1) can include an SQL database to store information about dispensation, enrolled patients, prescription, and doctors (clinicians). This data is served out to dispensers as described above and also to authorize users via Internet 68 using a web browser based interface as discussed below.

Figure 5A:
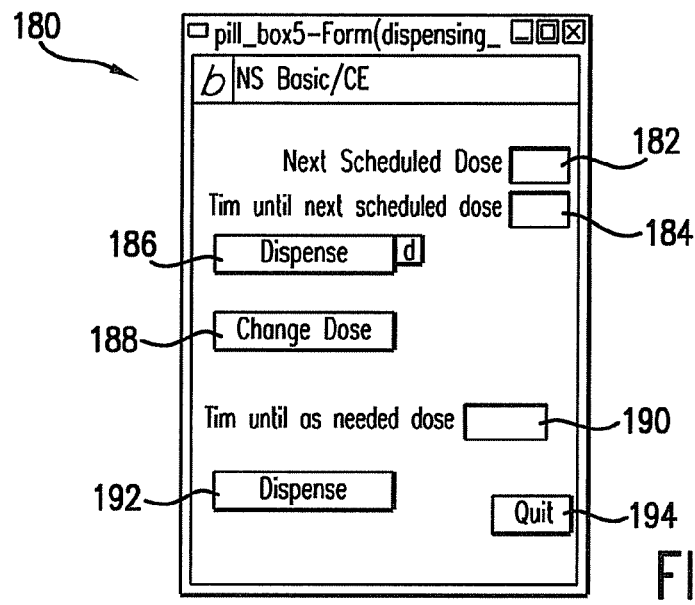
FIGS. 5A-5E illustrate interactive screen display windows used for user interaction with a controller of an embodiment of a system for a point-of-use medication control according to the present subject matter.
Figure 5B:
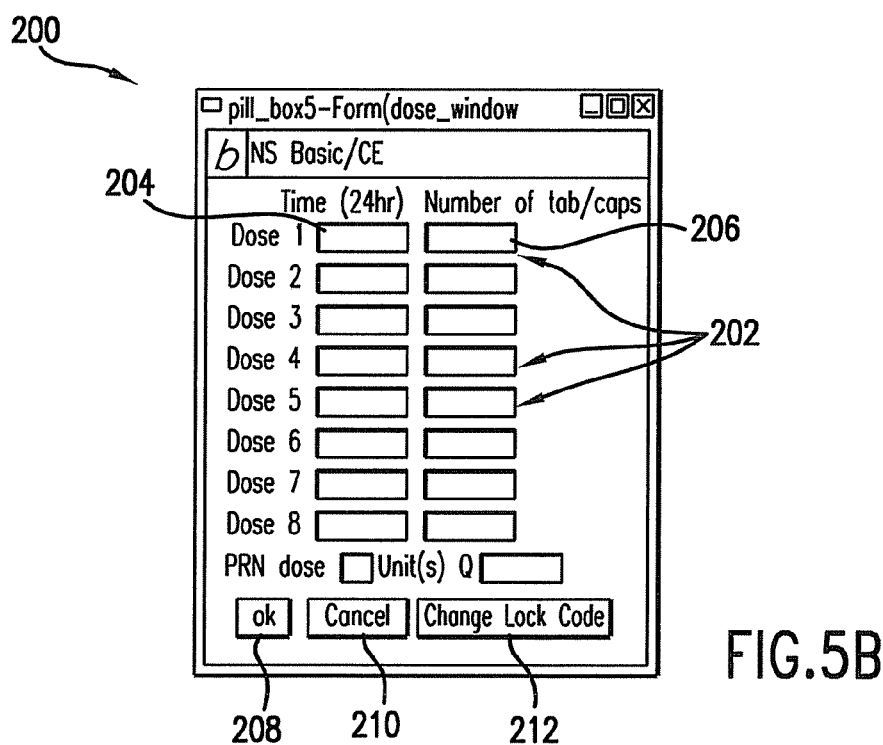

For embodiments which use a graphical user interface that is displayed on the display screen 32 of the controller 30, the user interface requires very little input from the patient. As shown in FIG. 5A, a dispensing window 180 shows a cell 182 for the next medication dose and a countdown timer cell 184 for that dose. The top dispense button 186 provides a button to dispense the regularly scheduled medication dose. However, the regularly schedule dose can be dispensed through other mechanisms such as by verifying the identity of the patient through an identification verification device. The change dose button 180 is not for use by the patient but is used by the doctor, pharmacist and/or the administrator of the out-patient medication system. Such a change dose button 188 is code locked.

Extra doses which can be provided for certain ailments such as migraines, anxiety, and pain medications, can be handled by the bottom half of the window 180. A countdown timer cell 190 shows when an extra dose is or will be available. The second dispenser button 192 activates the dosing cycle. The quit button 194 can be provided to end the dispensing program.

A dosing window 200 illustrated in FIG. 5 is provided for pharmacy access to medication directions. The window 200 is code locked to prevent access by unauthorized users. The window 200 can be accessed through the dispensing window 180 after the correct access code has been entered. Ideally, only the pharmacy has the correct code to unlock and gain access to the dosing window 200 as shown in FIG. 5B. The dosing window 200 includes dosing cells 202 that provide the time identifier 204 for each dose as well as amount identifier 206 for each dose. In this manner, scheduling time for each dose can be set by the pharmacist before dispenser 20 leaves the pharmacy. Approval button 208 is provided to approve the dosing schedule provided in dosing cells 202 once a scheduled time and dosage has been entered. A cancel button 210 permits canceling of the dosing schedule provided in dosing cells 202. In the embodiment shown, eight dosing cells 202 are provided, but not all of these cells 202 need to be used. For example, only four doses can be necessary within a 24 hour period. Thus, only four sets of dosing cells will need to be used. Further, if necessary, more dosing cells 202 can be provided.

A change lock code button 212 can be provided to change the lock code needed to gain access to the dosing window by the pharmacist. Dosing window 200 does not have to be used by the pharmacist. The controller of the system can be easily programmed via internet access to the central database which then can be communicated to the controller contained within the dispenser in the care of the patient. In the event that the internet access is unavailable, dosing window 200 allows programming access to authorized individuals.

Figure 5C:
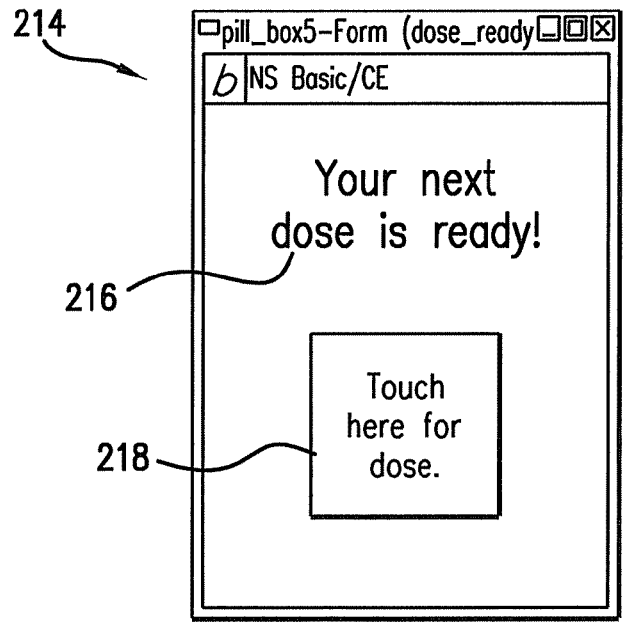

FIG. 5C illustrates dosing ready window 214 that alerts the patient that the medication is ready to be taken. As noted above in regards to the dose ready window shown on screen 32 of FIG. 1, the alert can include the activation of a signal light, tone, vibration, or voice prompt, thereby providing both visual and audio signals to alert the patient that a dose is ready. The dose ready window 214 can include a message 216 which alerts the patient to the fact that a dose is ready. Further, the dose ready window 214 can include an acknowledgement button 218 that can be activated to acknowledge receipt of the signal and thereby prompt the user to engage the finger sensor for activation of the dispenser to provide a dose of the medication.

Figure 5D:
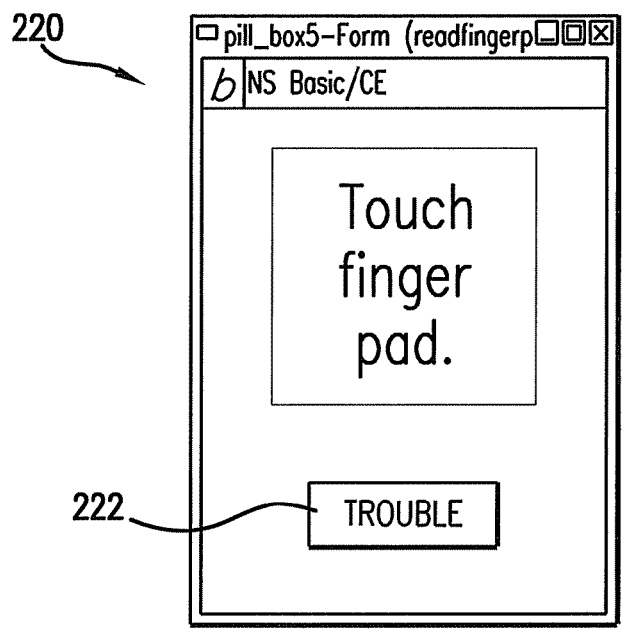

Once the signal screen shown in FIG. 5C is acknowledged through touching of the acknowledgement button 218, a fingerprint reading window 220 as shown in FIG. 5D can be displayed on display 32 to prompt the patient to touch a fingerprint sensor for positive identification of the patient before dispensing of the dose of medication. The fingerprint sensor provides rapid, reliable, and easy use and demands very little of the patient. Use of this identification verification device verifies that the patient is present at the time the medication is made available. The sensors on the system further check to see that the dose is picked up. While the system does not guarantee that the medication goes from hand to mouth of the patient, it can eliminate every barrier except willful refusal. If the patient is having trouble then a trouble button 222 can be provided that serves to trigger a transmission to a central database that technical support is needed. If finger reading proves to be a persistent problem, the use of the fingerprint reader can be bypassed.

Figure 5E:
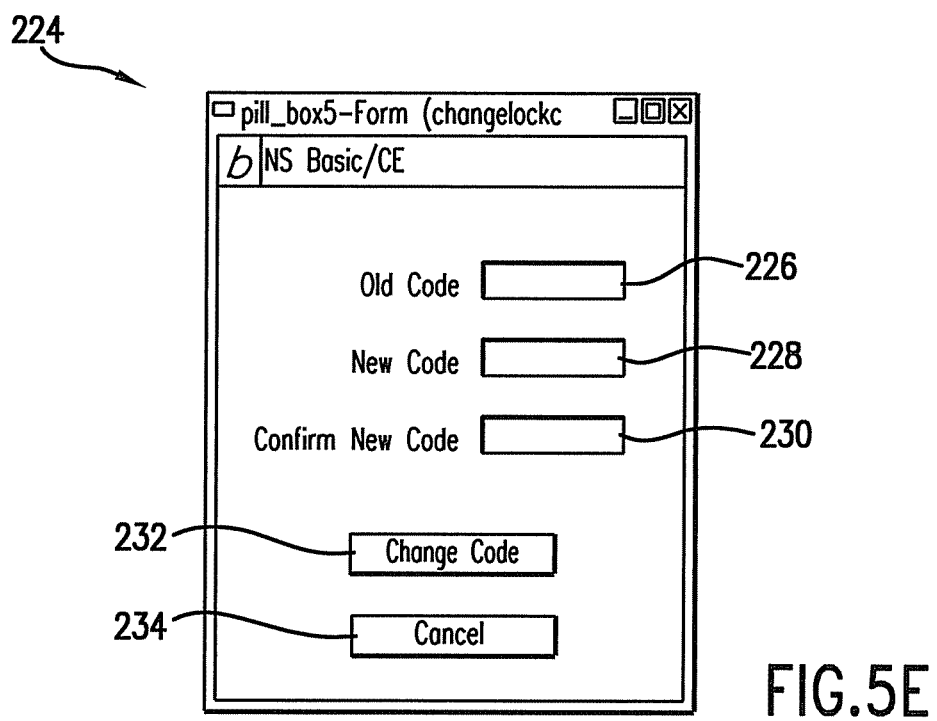

Further, the display window can provide a graphical user interface for changing the lock code as shown in FIG. 5E. A change lock code window 224 provides the ability of the pharmacist to change the lock code to prevent unauthorized access to the dosing window which can be used to alter the dosing schedule and amounts of the dosing of the medication. Change lock code window 224 can include cells to enter the old code at cell 226, enter a new code at the new code cell 228 and confirm the new code at confirmation cell 230. Once the new code is typed into both the new code cell 228 and confirmation cell 230, a change code button 232 can be activated to change the lock code. Thereby, the old code can be changed to a new code that controls the access to the dosing window 200. If the code typed into the new code cell 228 and confirmation code 230 do not match, the new code must be re-entered in both cells 228, 230. If the pharmacist does not wish to change the code, a cancel button 234 is provided to close the change code lock window 224.

A server can be used to store a database program that can include the central database 72 as shown in FIG. 1. For example, an Apple G5 server available from Apple Computer, Inc., of Cupertino, Calif., can run OpenBase 9.0, an SQL database program, available from OpenBase International, Ltd., of Concord, N.H., that can comprise the central database. An example of a structure of database 72 is shown in FIGS. 6-13. In particular, an array table database structure is described, although it is to be understood that other common forms of databases can be used. Further, different data can be collected, stored and used within the Database 72 other than the specific examples shown in FIGS. 6-13. FIGS. 6-13 are screen shots of a user interface for the database. Database 72 holds and distributes information on the doctors, patients, prescriptions, pharmacist, and dispenser units. Within the screen shots of FIGS. 6-13, different verbiage and words can be used to describe the same item. For example, dispensers can be called "trackers" within the screen shots of the particular embodiment of the database. Also, doctors and/or pharmacist can be identified by the term "Clinicians." The data interconnections can be shown within the Figures. The data fields of each table are also listed. Fields can be added or removed as needed. These changes are dynamically added to the web interface.

Figure 6:
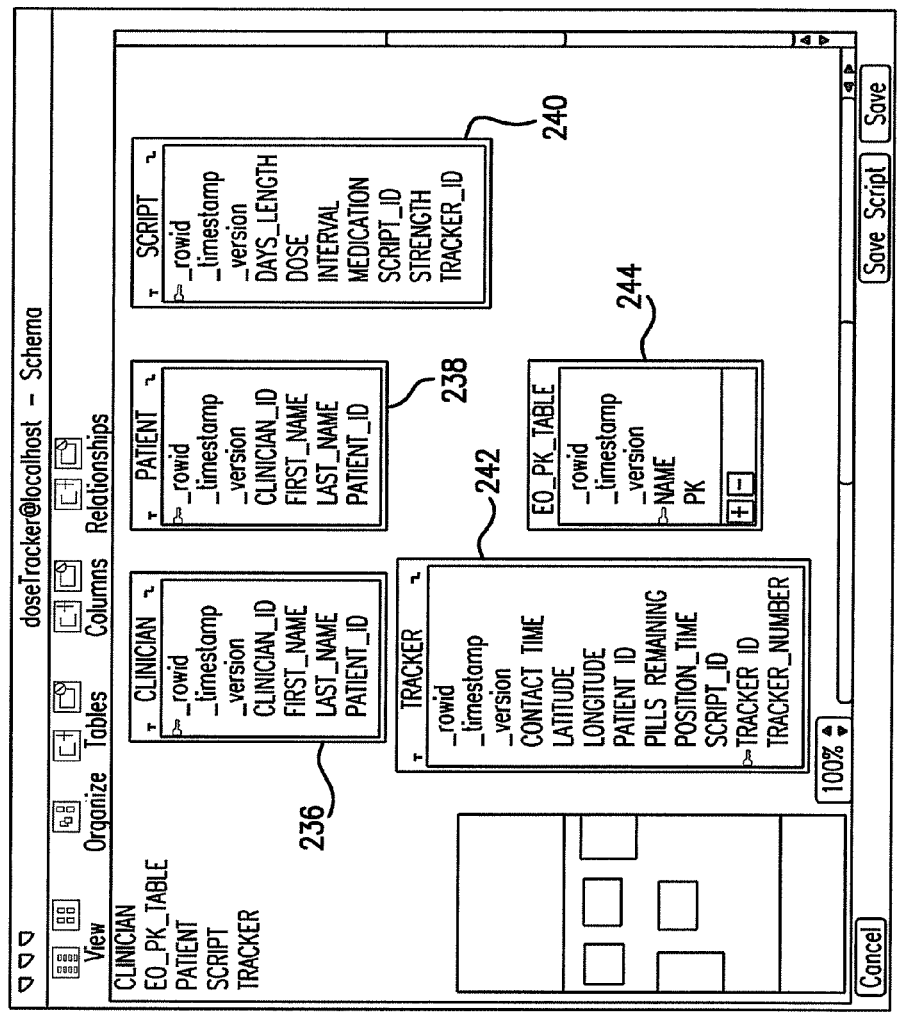
FIG. 6 illustrates a schematic representation of embodiments of possible data tables used within a database of an embodiment of a system for a point-of-use medication control according to the present subject matter.

As shown in FIG. 6, an array table can be provided for the clinician, patient, script, tracker, and EO_PK_table. These array tables contain different interconnected information. A clinician table 236 can include fields for the row ID, time stamp, version, clinician ID, the first name and last name of the clinician and patient ID. Similarly, a patient table 238 can have the fields for the row ID, time stamp, version, clinician ID, the first name and last name of the patient and patient ID. A script table 240 can include fields for row ID, time stamp, version, length of time in days, dose amount, the interval between doses, the medication, the script ID, the strength level of the medication, and tracker ID for each dispenser. Script table 240 can include information that would appear on a prescription or prescription bottle. A tracker table 242 corresponds to the information about the dispenser used by the patient. The fields of the tracker table 242 include row ID, time stamp, version, contact time, patient ID, pills remaining, script ID, tracker ID for each dispenser, and tracker number for each dispenser. Also, the fields within the tracker table can also include longitude and latitude of the dispenser provided by a location determination device, such as a GPS device, within the dispenser as well as the position time also provided by the location determination device within the dispenser.

The EO_PK_table 244 includes a row ID, time stamp, version, name, and primary key information. The EO_PK_Table is a database programming table used in setting up enterprise objects and primary keys within the database. The EO_PK_Table can be used to verify access to different data and is used to assign primary key attributes to the data entered and aids in placement within the right tables. The EO_PK_Table is automatically generated by the database software.

The EO_PK_Table may not be necessary depending on the database software and structure used.

Figure 7:
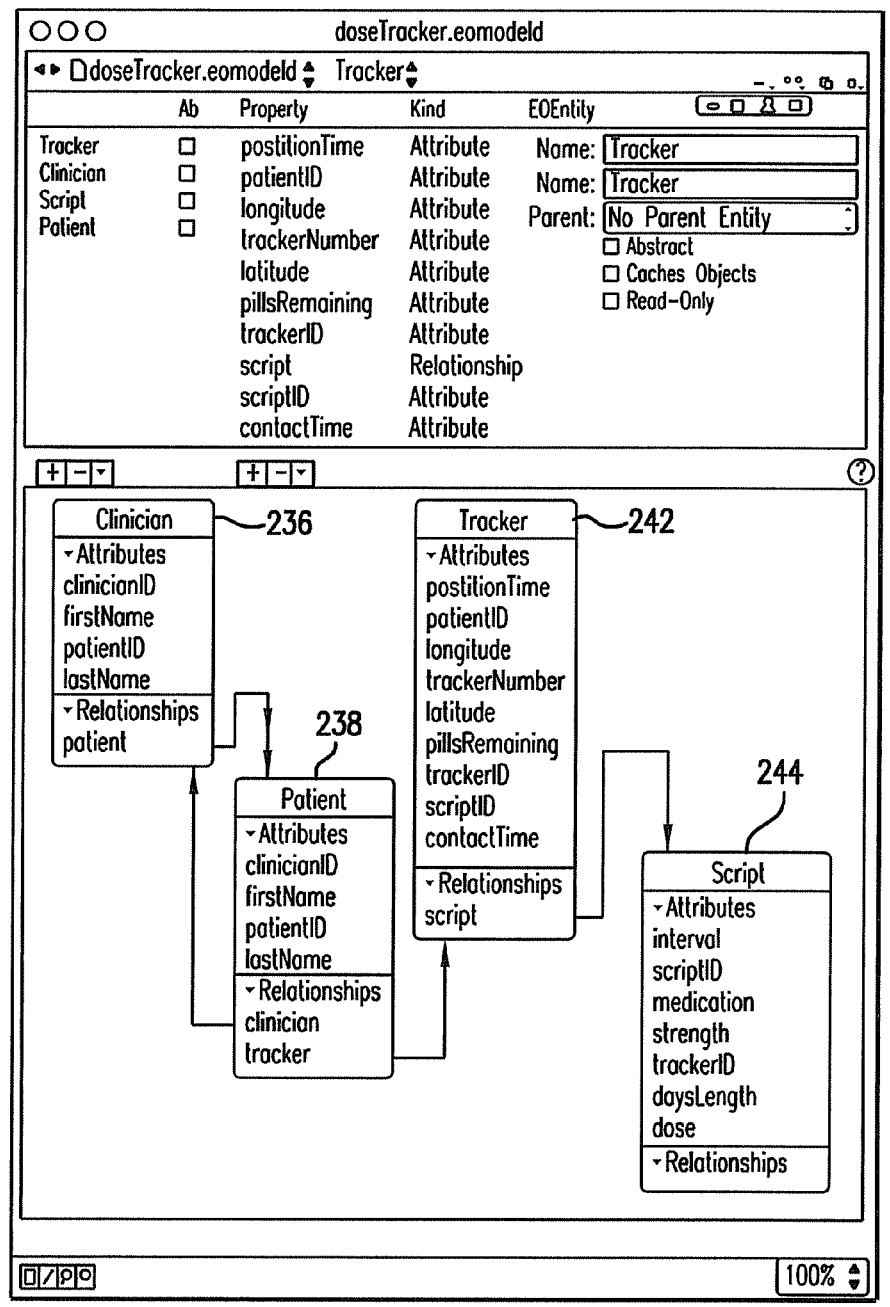
FIG. 7 illustrates a schematic representation of interactions between the data tables of FIG. 6.
Figure 8:
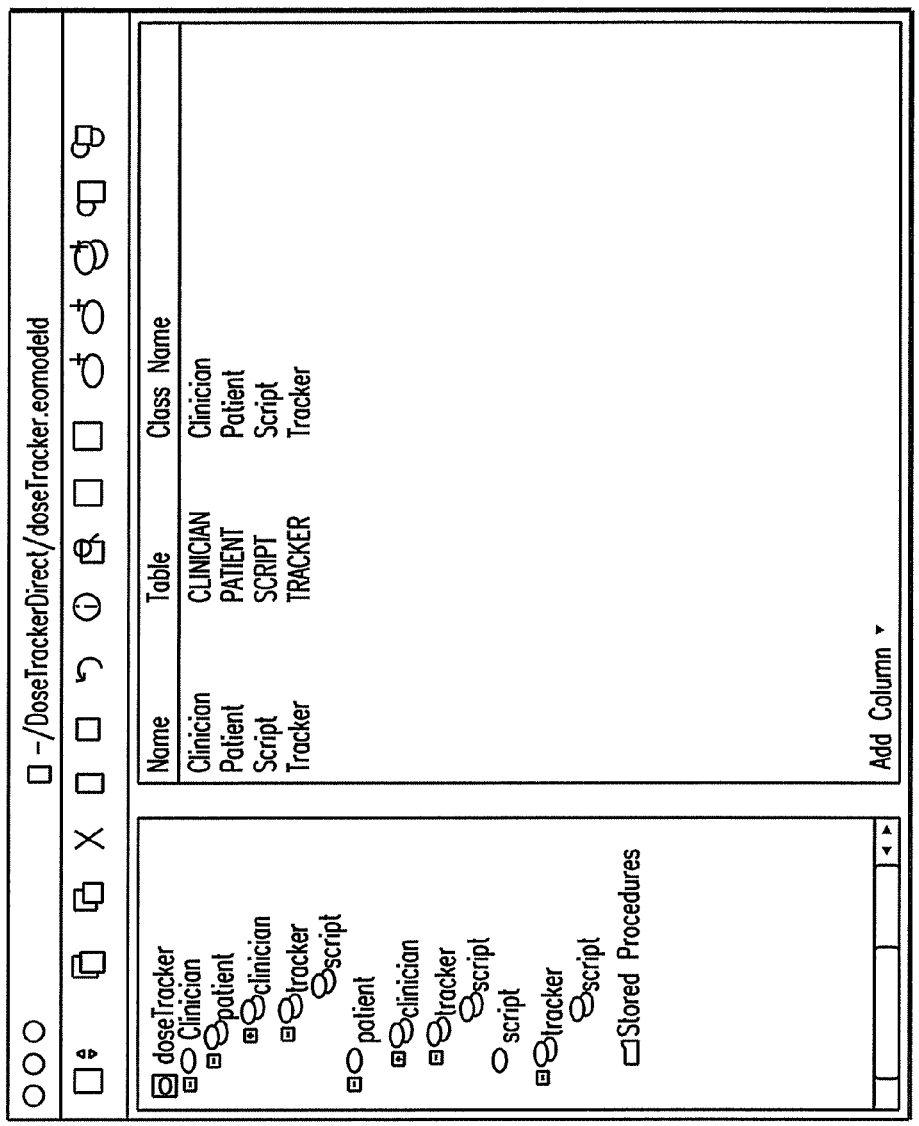
FIG. 8 illustrates a screen of a database that employs the data tables of FIG. 6.
Figure 10:
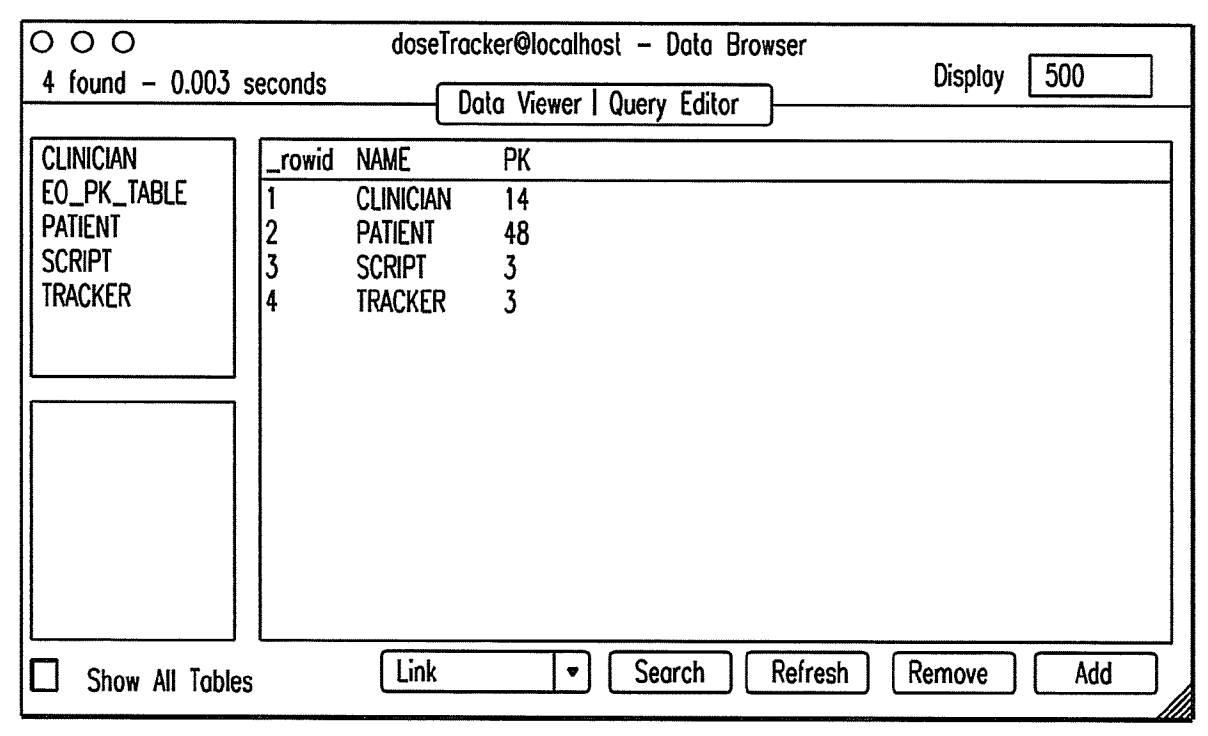

FIG. 7 shows the shared data fields and relationships between the different tables. For example, information is shared between clinician table 236 and patient table 238. Patient table 238 also shares information with tracker table 240 which in turn shares information with script table 242. In this manner, when certain information is updated within one of the tables, this information can be passed on to other associated tables. FIG. 8 shows a screen shot of an upper level screen which identifies the different tables by class names and names. FIGS. 9 and 10 show screen shots of data view information. In particular, FIG. 9 illustrates a clinician table identifying the clinician by the clinician's ID and his or her first and last name. FIG. 10 illustrates the top most level of the database.

FIG. 11 shows a patient table which identifies the patient by his or her first and last name in the fourth column and patient ID in the fifth column. The patient table provides a column for clinician ID to identify the clinician for each patient. Each row contains specific information for the patient within that row and assigns each patient a patient ID number displayed in column 6.

Figure 12:
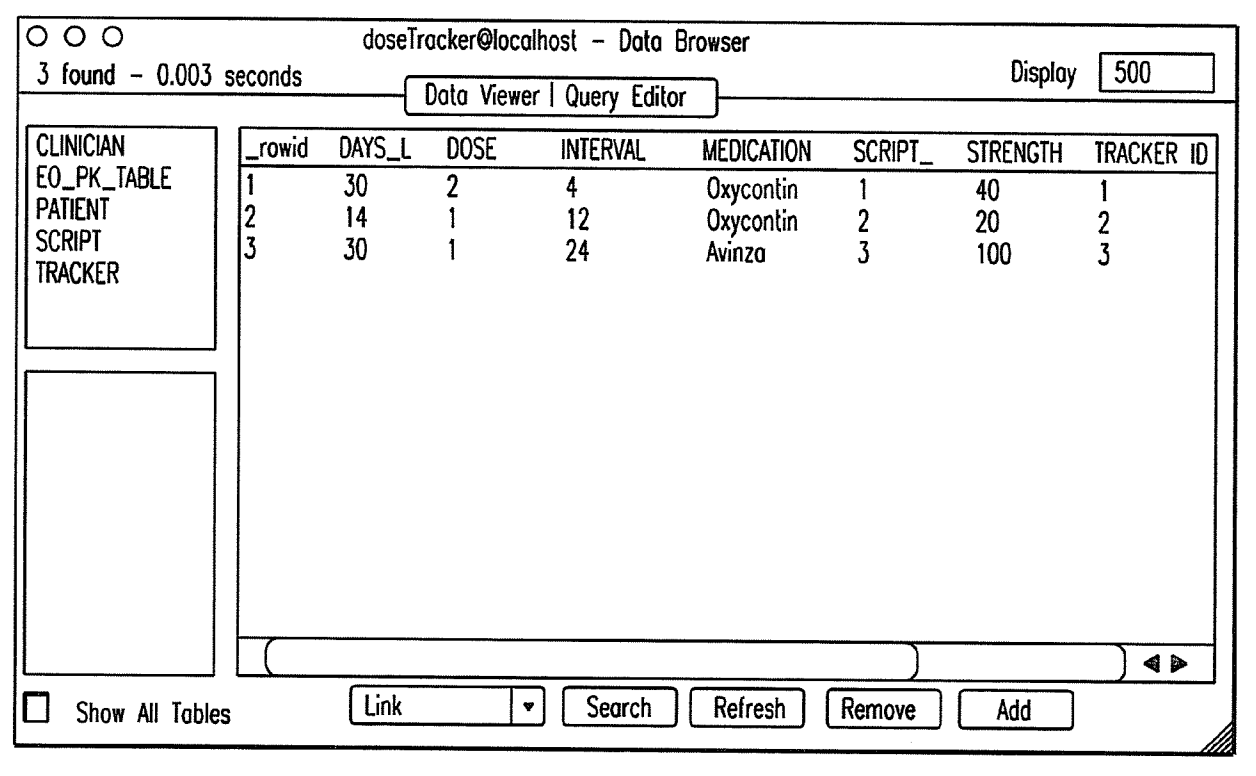

FIG. 12 shows a script table which identifies the number of days for which the medicine in each row is to be taken and the amount of the dose to be given as well as the interval measured in hours between doses. The script table also provides the name of the medication being administered and the strength of the medication. The script ID is provided as well as the tracker ID which is used to administer and dispense the associated medication at the appropriate doses and intervals. The Script table can also include information on each dose scheduled to be taken within a 24 hour period instead of relying just on the interval information. This would allow for greater dosing flexibility. Information regarding the amount of time that a dose will be available after it is due can be provided in the Script table. Further, lock out times can be provided that set the minimum time between doses. For example, if the lock out time is set at one hour and an optional dose is taken, then the next dose would not be available until after an hour of taking that optional dose. Information can also be provided as to the number of tablets or capsules dispense for each dose or optional dose requested. Also, the time interval between optional doses can be provided in the Script table.

Figure 13:
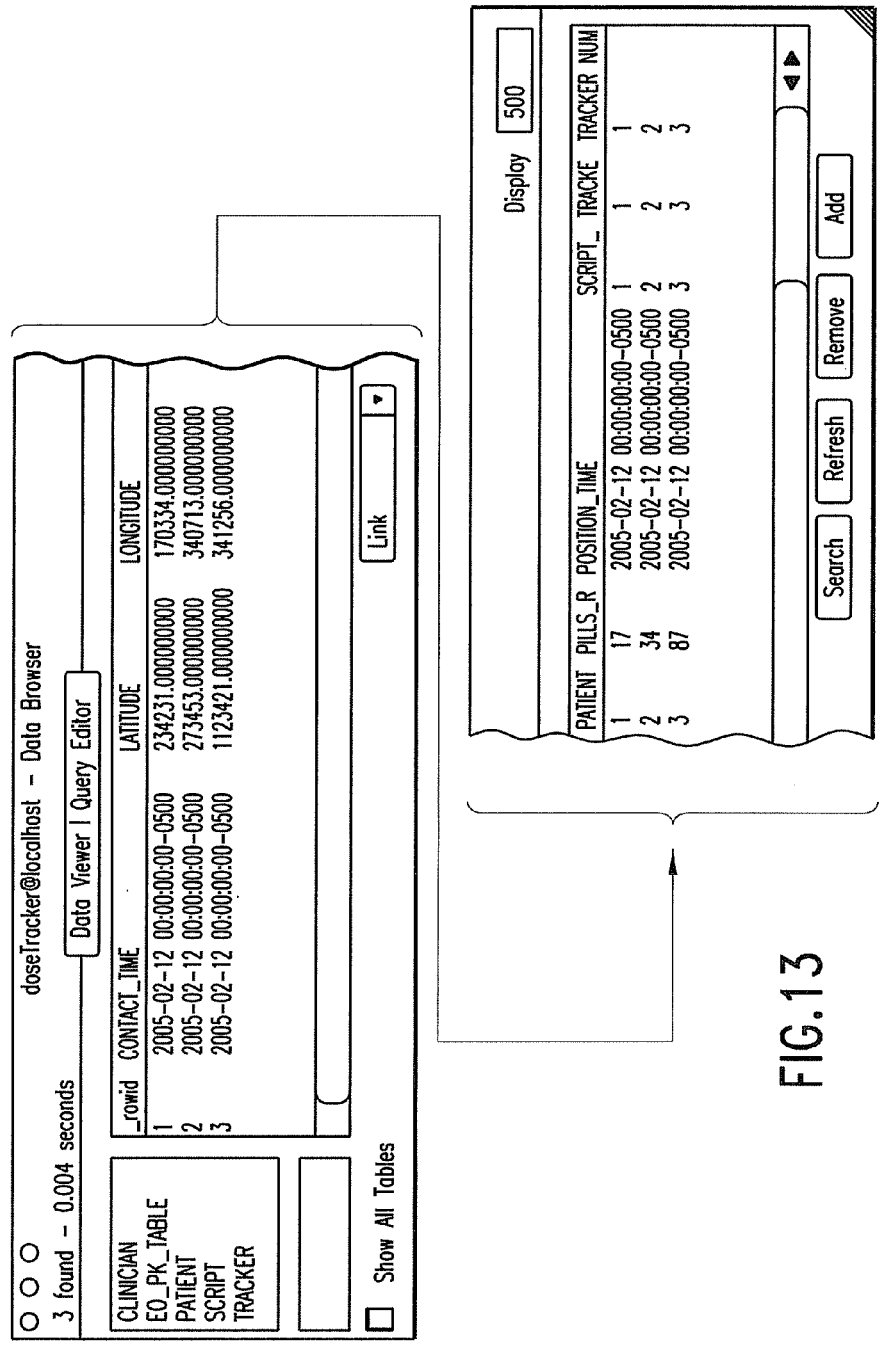
FIG. 13 illustrates a screen of a database that employs the data tables of FIG. 6.
Figure 23:
FIG. 23 illustrates, an interactive screen display window used for an internet web browser interface for a database of an embodiment of a system for a point-of-use medication control according to the present subject matter.

FIG. 13 illustrates a tracker table which identifies the row ID and contact time. The contact time provided is the last time the dispenser had contact with the database to exchange information. The tracker table shows the longitude and latitude of each tracker whose information is contained within the data field. The tracker table also provides columns for the patient ID for the patient and the number of pills remaining. The position time in which the position of each dispenser was last communicated to the database is also provided. The Script ID links the dispenser to its prescription. Tracker ID for each dispenser as well as a tracker number and script ID are provided within the tracker table for each dispenser. The tracker table can include other information, including dose history that can have a text summary of the times and status of each dose. The dose history of optional doses can be included as well. Further, information as to the time of the last dose dispensing and time of the last optional dose dispensing can also be included in the Tracker table or other tables.

As stated above, different database structures can be used with different information being provided. For example, database structures such as hierarchical models, network models, relational models, object models, relational-object models, or the like, can be used. Further, while database 72 is shown at a remote facility, database 72 can also be store on the memory of the controller of the system, if the controller has a large enough capacity.

The clinicians in the form of doctors and/or pharmacist, as well as the medication system administrator can have access to various tables within the database. Further, the patient can have limited access to certain information contained within the database. The clinicians, doctors, pharmacist, administrators and patients can have access to the database through an internet web browser interface as previously discussed. The browser based web interface can be provided by an Apple G 5 server or in the Apache web server with web objects acting on the application server. Such internet web browser interfaces essentially make the central database accessible to users and to controllers on the dispensers through the internet.

FIGS. 14 through 23 illustrate embodiments of screen shots which a user would encounter through an internet web browser interface. In particular, the screen shots illustrate screens that would be seen by an administrative level user progressing through the database. FIG. 14 illustrates a login screen which requires the input of a user name and password. An assistant box can be checked in order to identify the person logging into the system as an assistant. Once the user name and password have been entered, the user can click on the login button. This login screen provides a secure access to the data to authorized individuals.

FIG. 15 shows a next level screen that provides access to the different data tables to the administrator user. In particular, FIG. 15 shows a web search page that can be accessed from any web browser. For example, the administrator user can gain access to the clinician table, the patient table, the script table, or the tracker table from this page. The administrator user can look up specific data by using the scroll mechanism provided to look up the different fields within each data table. For example, the user can look up information by last name for the clinician or patient by entering in the specific last name for the clinician or the patient on which the user is trying to retrieve information. Further, the user may be able to find information within the script table. For example, the user can look up information in the field for medication within the script table. Another example can be to look up information within the tracker table related to a certain tracker number by entering the tracker number within the space provided in the cell for the tracker table. Each field within each different table can be searched in this manner. The scroll button beside the field enter cell allows the user to scroll through the different fields. Further, the relationship of what you are trying to search can also be changed. Instead of having information pulled up for the clinician's last name, the "equal sign" can be changed to a "not equal sign", thereby pulling up information on every clinician that does not have the specified last name. In this manner, a variety of ways of searching the different tables within the database can be accomplished through the web browser.

Once in the data table, links can be followed to other related tables. At each level, data editing is possible. Different levels of access are provided for each type of user. Doctors can only see their own patients listed. Similarly, pharmacies would only see information on their customers listed. Doctors would be allowed to modify their own patients dosing schedule but no add patients or prescriptions. Similarly, pharmacies would be able to add prescriptions but not modify them. If dispensing units are distributed from a central location, only administrators would need to add patients, clinicians, or dispensers to the database. Privileges to add or modify data entries could be assigned to fit individuals. FIGS. 16 through 23 illustrate different information that could be edited within the different tables by an administrative user.

No screen for controller to server communications is illustrated since these communications occur using machine-to-machine protocols. Simple object access protocol ("SOAP") calls are used to exchange XML packets between the dispensers and the database server. Contacts are initiated by the controllers of the dispensers when needed or at timed intervals. The controllers transmit their status of the dispensers and can accept new programming or data (including fingerprint templates for new users). As is evident from the screen shot of the dispensers (trackers data) in FIG. 21, position information is also transmitted. This would allow recovery of lost or stolen units.

The embodiments of the present disclosure shown in the drawings and described above are exemplary of numerous embodiments that can be made within the scope of the following claims. It is contemplated that the configurations for the devices, systems and methods for point of use medication control in the out-patient setting can comprise numerous configurations other then those specifically disclosed. Thus, it is intended that the scope of the patent issuing herefrom will only be limited by the scope of the pending claims.

What is claimed is:

1. A system for controlling dispensing of medication directly to an identified individual that is the intended recipient of the medication, the system comprising:
   a personal dispenser configured for holding and delivering at least one dose of medication directly to an identified individual that is the intended recipient of the medication, wherein the dispenser comprises:
      a vacuum mechanism for creating a vacuum suction to deliver the dose of medication from within the dispenser to the identified individual that is the intended recipient of the medication,
      a sealable pill magazine for storing units of medication,
      a dispensing well in communication with the pill magazine to permit transfer of the units of medication from the pill magazine to the dispensing well, the dispensing well have an opening therein to permit removal of units of medication therefrom,
      a shutter movably positionable proximate to the opening of the dispensing well, the shutter being movable between an open position in which access through the opening of the dispensing well is permitted and a closed position in which the opening of the dispensing well is closed, and
      a vibrator positioned against the pill magazine;
   a controller operatively connected to the dispenser, wherein the controller automatically operates the dispenser for movement to a dispensing position at a predetermined time, wherein the controller is programmable with a medication dispensing program which includes a data store comprising the predetermined time to operate the dispenser and the name of the at least one dose of medication, wherein the controller is configured for emitting a signal indicating to the identified individual that is the intended recipient of the medication that it is time to dispense a dose of medication from the dispenser at the predetermined time;
   an electronic communication device for connecting the controller to a remote facility;
   an identification verification device for controlling access to the system by the identified individual that is the intended recipient of the medication; and
   a location determination device for determining the location of the dispenser.

2. The system according to claim 1, further comprising at least one of a speaker or a display screen, wherein the signal of the controller is an audible signal that can be emitted by the internal speaker, a visual signal that can be displayed on the display screen, or a combination thereof.

3. The system according to claim 1, further comprising a response mechanism electronically connected to the controller such that the controller can be instructed that the signal has been received when the response mechanism is actuated.

4. The system according to claim 1, wherein the data store further comprises at least one of patient data, a patient compliance schedule, caregiver data, compliance notification data, pharmacy data, physician data, insurance data, or emergency contact data.

5. The system according to claim 1, wherein the controller is programmable to connect to a predetermined Internet Service Provider through the electronic communication device in order to transmit or receive at least one of patient data, pharmacy data, physician data, insurance data, or emergency contact data.

6. The system according to claim 5, wherein the controller is programmable to transmit an order requesting a refill of the at least one medication or the dispenser containing the at least one medication when the system is connected to the predetermined Internet Service Provider.

7. The system according to claim 1, wherein the controller is programmable to connect to a predetermined Internet Service Provider through the electronic communication device in order to transmit compliance schedule and compliance notification data and when the controller is not instructed within a predetermined time frame that the signal has been received, the controller transmits a non-compliance notification to the Internet Service Provider.

8. The system according to claim 7, wherein the controller is programmable to update and transmit the caregiver data and compliance notification data when the system is connected to the predetermined Internet Service Provider.

9. The system according to claim 1, wherein the identification verification device comprises a biometric identification device.

10. The system according to claim 9, wherein the identification verification device comprises a biometric identification fingerprint system.

11. The system according to claim 1, wherein the location determination device comprises an integrated Global Positioning System (GPS) receiver.

12. The system according to claim 1, further comprising an emergency assistance button electronically connected to the controller in such a manner that when the emergency assistance button is actuated, the controller is instructed to transmit an emergency message.

13. The system according to claim 1, wherein the vacuum mechanism is configured to enter through the opening of the dispensing well.

14. The system according to claim 1, wherein the pill magazine comprises a slanted base surface wall that extends into the dispensing well and against which the vibrator resides.

15. The system according to claim 1, wherein the pill magazine further comprises a fill door that can be opened to permit filling of the pill magazine and closed to deny access into the pill magazine therethrough and a tamper switch in communication with the fill door.

16. The system according to claim 1, further comprising a tilt sensor disposed within the dispenser.

17. A system for controlling dispensing of medication directly to an identified individual that is the intended recipient of the medication, the system comprising:
- a personal dispenser configured for holding and delivering at least one dose of medication directly to an identified individual that is the intended recipient of the medication, wherein the dispenser comprises:
  - a vacuum mechanism for creating a vacuum suction to deliver the dose of medication from within the dispenser to the identified individual that is the intended recipient of the medication,
  - a sealable pill magazine for storing units of medication,
  - a dispensing well in communication with the pill magazine to permit transfer of the units of medication from the pill magazine to the dispensing well, the dispensing well have an opening therein to permit removal of units of medication therefrom,
  - a shutter movably positionable proximate to the opening of the dispensing well, the shutter being movable between an open position in which access through the opening of the dispensing well is permitted and a closed position in which the opening of the dispensing well is closed, and
  - a vibrator positioned against the pill magazine;
- a controller operatively connected to the dispenser, wherein the controller automatically operates the dispenser for movement to a dispensing position at a predetermined time, wherein the controller is programmable with a medication dispensing program which includes a data store comprising the predetermined time to operate the dispenser and the name of the at least one dose of medication, wherein the controller is configured for emitting a signal indicating to the identified individual that is the intended recipient of the medication that it is time to dispense a dose of medication from the dispenser at the predetermined time;
- an electronic communication device for connecting the controller to a remote facility;
- an identification verification device for controlling access to the system to the identified individual that is the intended recipient of the medication;
- a location determination device for determining the location of the dispenser; and
- a lockout for disabling functionality of the system based upon a predetermined criteria.

18. The system according to claim 17, wherein the lockout comprises at least one of a breath sensor for determining a breath alcohol level and the predetermined criteria comprises a maximum breath alcohol level or an interactive cognitive test and the predetermined criteria comprises a minimum cognitive level.

19. The system according to claim 9, wherein the identification verification device comprises a biometric identification device.

20. The system according to claim 19, wherein the identification verification device comprises a biometric identification fingerprint system.

* * * * *